(12) United States Patent
Bachovchin et al.

(10) Patent No.: US 7,259,234 B2
(45) Date of Patent: Aug. 21, 2007

(54) STABLE ANALOGS OF PEPTIDE AND POLYPEPTIDE THERAPEUTICS

(75) Inventors: William W. Bachovchin, Melrose, MA (US); Hung-sen Lai, Winchester, MA (US); David George Sanford, Reading, MA (US)

(73) Assignee: Trustees of Tufts College, Medford, MA (US)

( * ) Notice: Subject to any disclaimer, the term of this patent is extended or adjusted under 35 U.S.C. 154(b) by 425 days.

(21) Appl. No.: 10/847,220

(22) Filed: May 17, 2004

(65) Prior Publication Data

US 2005/0049177 A1 Mar. 3, 2005

Related U.S. Application Data

(60) Provisional application No. 60/471,411, filed on May 15, 2003.

(51) Int. Cl.
*C07K 14/605* (2006.01)

(52) U.S. Cl. ............... 530/308; 514/2; 514/12; 530/324

(58) Field of Classification Search ............ None
See application file for complete search history.

(56) References Cited

U.S. PATENT DOCUMENTS

| | | |
|---|---|---|
| 5,118,666 A | 6/1992 | Habener |
| 5,120,712 A | 6/1992 | Habener |
| 5,276,137 A | 1/1994 | Ojima et al. |
| 5,545,618 A | 8/1996 | Buckley et al. |
| 5,614,492 A | 3/1997 | Habener |
| 5,766,620 A | 6/1998 | Heiber et al. |
| 5,958,909 A | 9/1999 | Habener |
| 5,994,500 A | 11/1999 | Drucker et al. |
| 6,184,201 B1 | 2/2001 | Drucker et al. |
| 6,268,343 B1 | 7/2001 | Knudsen et al. |
| 6,277,819 B1 | 8/2001 | Efendic |
| 6,358,924 B1 | 3/2002 | Hoffmann |
| 6,489,295 B1 | 12/2002 | Drucker et al. |
| 2001/0011071 A1* | 8/2001 | Knudsen et al. ............... 514/12 |
| 2004/0242853 A1* | 12/2004 | Greig et al. ................. 530/399 |

FOREIGN PATENT DOCUMENTS

| | | |
|---|---|---|
| WO | WO99/40788 A1 | 8/1999 |
| WO | WO99/43705 A1 | 9/1999 |
| WO | WO99/43706 A1 | 9/1999 |
| WO | WO99/43707 A1 | 9/1999 |
| WO | WO 00/07617 A1 | 2/2000 |
| WO | WO 01/98331 A2 | 12/2001 |
| WO | WO 02/22151 A2 | 3/2002 |
| WO | WO 02/46227 A2 | 6/2002 |
| WO | WO 02/47716 A2 | 6/2002 |
| WO | WO 02/069994 A2 | 9/2002 |
| WO | WO 03/002136 A2 | 1/2003 |
| WO | WO 03/018516 A2 | 3/2003 |

OTHER PUBLICATIONS

Mentlein et al., "Dipeptidyl-peptidase IV hydrolyses gastric inhibitory polypeptide, glucagon-like peptide-1(7-36) amide, peptide histidine methionine and is responsible for their degradation in human serum," *European Journal of Biochemistry*, 214(3):829-835 (1993).

Deacon et al., "Dipeptidyl peptidase IV resistant analogues of glucagon-like peptide-1 which have extended metabolic stability and improved biological activity," *Diabetologia*, 41(3):271-278 (1998).

Guarita, et al., "PYY Regulates Pancreatic Exocrine Secretion Through Multiple Receptors in the Awake Rat," *Digestive Diseases and Sciences*, 2000, vol. 45(9) 1696-1702.

Keire, et al., "Structure and receptor binding of PYY analogs," *Peptides* 23 (2002) 305-321.

Mentlein, Rolf, "Dipeptidyl-peptidase IV (CD26)-role in the inactivation of regulatory peptides," *Regulatory Peptides* 85 (1999) 9-24.

Naslund, et al., "Glucagon-like peptide-1 analogue LY315902: Effect on intestinal motility and release of insulin and somatostatin," *Regulatory Peptides* 106 (2002) 89-95.

\* cited by examiner

*Primary Examiner*—Anish Gupta
(74) *Attorney, Agent, or Firm*—Dana M. Gordon; Foley Hoag LLP

(57) ABSTRACT

The present invention relates to compositions of peptide and polypeptide analogs that are resistant to proteolysis, pharmaceutical uses thereof, and methods of preparation thereof.

6 Claims, 16 Drawing Sheets

Rapid Degradation of GLP-1 by DPP IV

– 2 min after intravenous admin.
– 30 min after subcutaneous admin.

Figure 4. Preliminary Characterization of 3-butyl-methyl-glycine GLP-1

Tertiary leucine (Tle) in position P'1 produces a peptide analog resistant to cleavage by thrombin WALAIR (SEQ ID NO: 33)
WALAPRSFA (SEQ ID NO: 31)
WALAPRSFA +Thrombin (SEQ ID NO: 31)
WALAPRXFA (SEQ ID NO: 32)
WALAPRXFA +Thrombin (SEQ ID NO: 32)

Figure 7

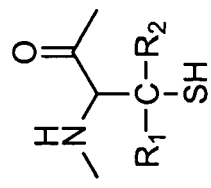 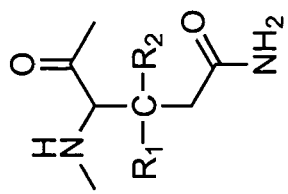 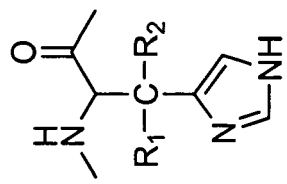
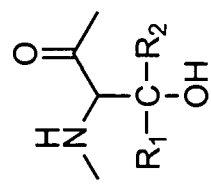 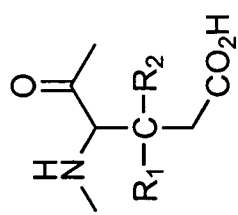 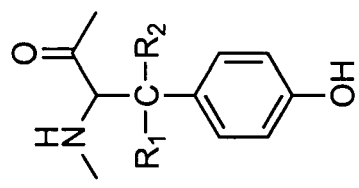
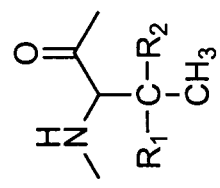 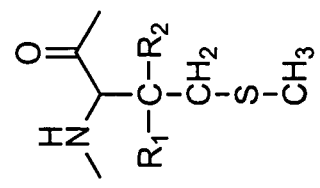 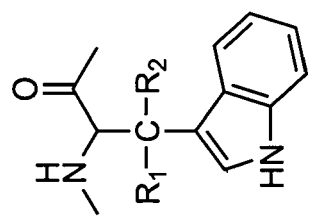
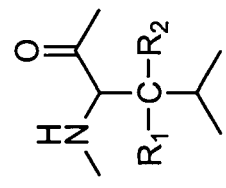 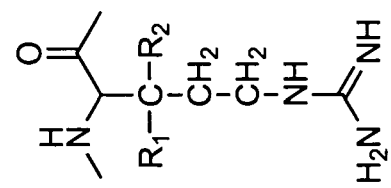 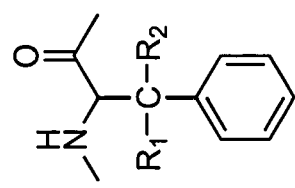
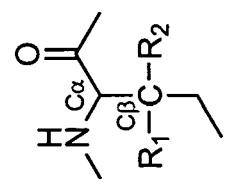 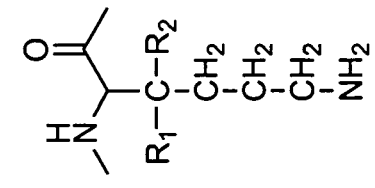 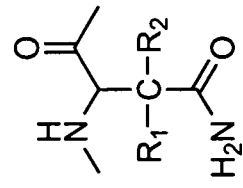
Figure 16

STABLE ANALOGS OF PEPTIDE AND POLYPEPTIDE THERAPEUTICS

CROSS-REFERENCE TO RELATED APPLICATIONS

This application claims the benefit of priority from U.S. Provisional Application No. 60/471,411, filed May 15, 2003, the specification of which is incorporated by reference herein in its entirety.

BACKGROUND OF THE INVENTION

Polypeptide and peptide therapeutics are widely used in medical practice. Their ease of production, either by recombinant DNA technology or peptide synthesizers, ensures their continued use in a variety of circumstances in the years to come. Accordingly, polypeptide therapeutics, such as hormones, cytokines and growth factors, represent an important class of therapeutic agents. Certain native polypeptides, however, can be inactivated rapidly in vivo via proteolysis or isomerization. Such inactivation can be inconvenient in cases where it is desired to maintain a consistent or sustained blood level of the therapeutic over a period of time, as repeated administrations are then necessary. In certain instances, one or more of the proteolytic products of the polypeptide can be antagonistic to the activity of the intact polypeptide. In these cases, administration of additional therapeutic alone may be insufficient to overcome the antagonist effect of the proteolytic products.

To further illustrate, one class of peptide hormones whose prolonged presence in the blood may be beneficial include glucagon-like peptides 1 and 2 (GLP-1 and GLP-2 respectively), glucose-dependent insulinotropic peptide (GIP), neuropeptide Y (NPY), pancreatic polypeptide (PP), and peptide YY (PYY). GLP-1 is an important polypeptide hormone with regulatory function in glucose metabolism and gastrointestinal secretion and metabolism. Current efforts show that GLP-1 is a growth factor for beta cells in the pancreas and perhaps is involved in cell differentiation in other organs as well. GLP-2 is a 33-amino acid peptide having therapeutic application in the treatment of diseases of the gastrointestinal tract. In particular, it has been determined that GLP-2 acts as a trophic agent to enhance and maintain proper gastrointestinal function, as well as to promote growth of intestinal tissues (See, e.g., U.S. patent Ser. Nos. 5,834,428; 5,789,379; and 5,990,077; and International Publication No. WO 98/52600). GIP is a 42-amino acid peptide synthesized and secreted from endocrine cells in the small intestine (See R. A. Pederson, et al., *Endocrinology* 99, 780-785 (1976) and T. B. Usdin, et al., *Endocrinology* 133, 2861-2870 (1993)). GIP infusions have been shown to inhibit the effects of glucagon on the liver while enhancing those of insulin. Additionally, GIP has dual effects on hepatic blood flow, increasing flow through the portal vein and inhibiting flow through the hepatic artery. Neuropeptide Y is a 36-amino acid member of the pancreatic polypeptide family. It is highly concentrated in both the central and peripheral mammalian nervous system, is the most potent substance known to cause an increase in feeding, and may play a role in the genetic basis of Type II Diabetes Mellitus (See U.S. Pat. Nos. 6,410,701, 6,075,009, 5,026,685, 5,328,899, and K. Tatemoto, Proc. Natl. Acad. Sci. USA 79, 5485-5489 (1982)). Peptide YY (PYY) and pancreatic polypeptide (PP) are structurally related peptide hormones involved in memory loss, depression, anxiety, epilepsy, pain, hypertension, and sleep and eating disorders.

These polypeptide hormones, and other polypeptide factors, are believed to be degraded by members of the post-proline cleaving class of serine proteinase enzymes, such as dipeptidyl peptidase IV (DPP IV). DPP IV is a membrane associated serine peptidase which cleaves N-terminal dipeptides from a peptide chain containing in the penultimate (P1) position, preferably, a proline residue, or an alanine residue if the N-terninal residue (P2) is histidine or a large aromatic such as tyrosine, tryptophan or phenylalanine. The amino terminus sequences of GLP-1, GIP, and GLP-2 are His-Ala-Glu, Tyr-Ala-Glu, and His-Ala-Asp respectively. The amino terminal sequences of NPY, PP, and PYY are Tyr-Pro-Ser, Ala-Pro-Leu and Tyr-Pro-Ile respectively. Hence, DPP IV has been implicated in the regulation of the activity of each of these polypeptide hormones, as well as other polypeptides, in vivo.

DPP IV-mediated removal of Xaa-Ala or Xaa-Pro dipeptides, wherein Xaa is an amino acid residue, from the N-terminus of the bioactive peptide hormones mentioned above renders them inactive, or even antagonistic. Accordingly, cleavage and inactivation of peptide hormones by serine proteinases such as DPP IV is just one example that illustrates the significant limitation imposed by proteolysis for the use of therapeutic polypeptides. The discovery of analogs that exhibit stability towards proteolysis, such as DPP IV-mediated inactivation, is therefore of substantial interest. Accordingly, there is a need in the art for proteolysis-resistant peptide hormones.

SUMMARY OF THE INVENTION

The present invention generally provides compositions of peptide or polypeptide analogs (herein "$P'_1$ analogs") that are resistant to cleavage by proteinases (e.g., analogs that are resistant to proteolysis).

One aspect of the invention relates to the discovery that modification of substrates for post-proline cleaving proteinases at the $P'_1$ position (the residue to the carboxy terminal side of the amide cleavage site) can produce substrate analogs with greatly reduce susceptibility to enzyme-mediated cleavage relative to the native substrate, yet retain the biological activity of the native substrate. For example, modification of substrates of the post-proline cleaving serine proteinase DPP IV with an amino acid analog at the $P'_1$ residue (of the DPP IV cleavage site) results in a substrate analog with reduce susceptibility to cleavage by DPP IV, yet retains the biological activity of the underlying substrate.

Another aspect of the invention relates to the more general observation that modification of proteinase substrates at the $P'_1$ residue (of the cleavage site) with an amino acid analog having a tetrasubstituted Cβ carbon can markedly increase the in vivo half-life of the resulting analog, e.g., which may have a longer duration of biological action and/or reduced clearance relative ot the wild-type polypeptide. Based on this discovery, and its applicability to substrates cleaved by a diverse range of proteinases, the present invention provides a method for producing $P'_1$ analogs of substrates for such proteinases as serine proteinases, metalloproteinases, aspartic proteinases, and cysteine proteinases.

The present invention also provides pharmaceutical compositions comprising one or more of the subject "$P'_1$ analogs". Exemplary pharmaceutical compositions comprise one or more $P'_1$ analogs formulated with pharmaceutically acceptable carriers or excipients.

Another aspect of the present invention is a method of treating a disease in a subject comprising administering a therapeutically effective amount of one or more of said $P'_1$ analogs. The subject P'₁ analogs can be administered alone, or can be administered as part of a therapeutic regimen including other therapies appropriate to the specific disease indication. By way of example, administration of a P'₁ analog for the treatment of diabetes may be used alone, or may be used in combination with modulation of diet and exercise, and/or with administration of insulin. Further exemplary combinatorial methods of treatment comprise administration of a P'₁ analog and administration of an inhibitor of the particular enzyme that cleaves the native polypeptide. Such an inhibitor may be specific to the particular enzyme (e.g., a DPP IV specific inhibitor) or may be more generic to the enzyme class (e.g., a serine protease inhibitor).

Another aspect of the present invention is use of the subject P'₁ analogs for diagnostic purposes.

Another aspect of the present invention is use of the subject P'₁ analogs for the manufacture of a medicament for providing proteinase resistant peptides.

Another aspect of the present invention is use of a P'₁ analog in the manufacture of a therapeutic medicament.

Yet another aspect of the present invention is a method of conducting a business comprising, identifying, manufacturing, marketing, distributing, and licensing a P'₁ analog, pharmaceutical compositions thereof, and/or kits including the P'₁ analog.

In any of the foregoing aspects, the present invention contemplates compositions and methods wherein the P'₁ analog is an analog of a polypeptide hormone such as glucagon-like peptide, NPY, PPY, secretin, GLP-1, GLP-2, and GIP. However, the present invention recognizes that any polypeptide or peptide hormone that is cleaved by a proteinase may be modified at the cleavage site as described herein to provide P'₁ analogs that are resistant to proteolysis. Furthermore, the present invention recognizes that P'₁ analogs resistant to any of a number of classes of proteinases can be readily designed based on our knowledge of the cleavage site of those enzymes and based on the teachings of this application. Exemplary classes of proteinases include metalloproteinases, aspartic proteinases, cysteine proteinases, and serine proteinases.

BRIEF DESCRIPTION OF THE FIGURES

FIG. 7 shows that substitution of a tertiary-leucine (TLE) at the P'1 position of a model peptide substrate for the serine protease thrombin results in the production of a peptide analog resistant to cleavage by thrombin.

FIG. 16 shows exemplary embodiments of Formula (II), wherein naturally occurring amino acids have been modified at the β-position (3-position) with $R_1$ and $R_2$.

DETAILED DESCRIPTION OF THE INVENTION

I. Overview

Figure 1:
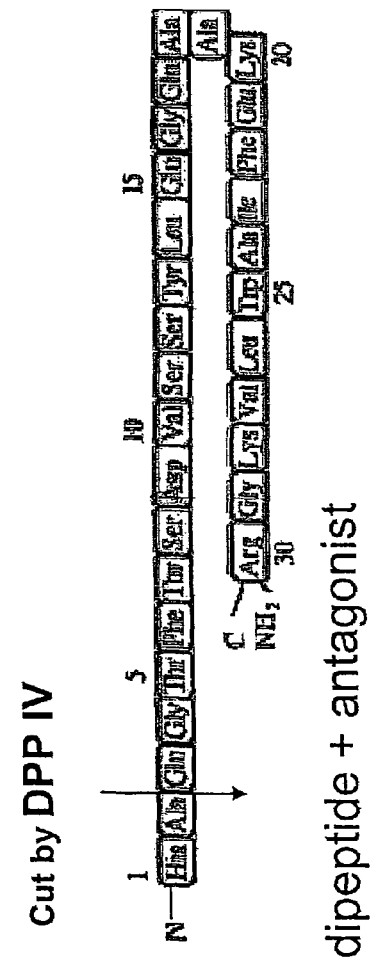
FIG. 1 shows a schematic of the degradation of a native GLP-1 by DPP IV.

The present invention generally relates to peptide and P'₁ analogs that have increased in vivo half-lives, e.g., resulting from reduced susceptibility to cleavage by proteolytic enzymes, yet retain the desired acivity of the original substrate. The P'₁ analogs of the present invention include analogs of growth factors, cytokines, peptide hormones and other polypeptides and peptides whose activity and/or half-life in vivo are ordinarily regulated by proteolytic cleavage.

One aspect of the invention relates to the discovery that modification of substrates for post-proline cleaving proteinases at the P'₁ position (the residue to the carboxy terminal side of the amide cleavage site) can produce substrate analogs with greatly reduce susceptibility to enzyme-mediated cleavage relative to the native substrate, yet retain the biological activity of the native substrate. For example, modification of substrates of the post-proline cleaving serine proteinase DPP IV with an amino acid analog at the P'₁ residue (of the DPP IV cleavage site) results in a substrate analog with reduce susceptibility to cleavage by DPP IV, yet retains the biological activity of the underlying substrate.

While replacing the P'₁ residue with another naturally occurring amino acid is contemplated, in preferred embodiments, the P'₁ residue is replaced with a non-naturally occurring amino acid analog, and even more preferably, with one which is a structural analog, e.g., retaining similar attributes with respect to steric and/or electronic nature. To illustrate, in certain embodiments the present invention provides a modified polypeptide which is rendered less susceptible to proteolysis by a post-proline cleaving proteinases, such as dipeptidylpeptidase IV (DPP-IV), wherein the polypeptide has been modified at the P'₁ position with an amino acid or amino acid analog of Formula I:

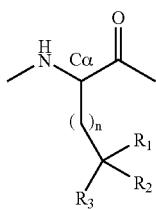

wherein,

R₁ and R₂ are independently selected from lower alkyl, heteroalkyl, cycloalkyl, heterocycloalkyl, aryl, heteroaryl, alkoxyl, carboxyl, carboxamide, carbonyl, halogen, hydroxyl, amine, or cyano, or R₁ and R₂ taken together form a ring of 4-7 atoms;

R₃ is selected from lower alkyl, heteroalkyl, cycloalkyl, heterocycloalkyl, aryl, heteroaryl, amino, alkoxyl, halogen, carboxyl, carboxamide, carbonyl, cyano, thioalkyl, acylamino, amido, cyano, nitro, azido, sulfate, sulfonate, sulfonamido, —(CH₂)$_m$R₄, —(CH₂)$_m$OH, —(CH₂)$_m$COOH, —(CH₂)$_m$O-lower alkyl, —(CH₂)$_m$O-lower alkenyl, —(CH₂)$_n$O(CH₂)$_m$R₄, —(CH₂)$_m$SH, —(CH₂)$_m$S-lower alkyl, —(CH₂)$_m$S-lower alkenyl, —(CH₂)$_n$S(CH₂)$_m$—R₄, (CH₂)$_m$NH₂, —(CH₂)$_m$NC(=NH)NH₂, —(CH₂)$_m$C(=O)NH₂, or —(CH₂)$_m$NH₂,;

R₄ represents, independently for each occurrence, aryl, aralkyl, cycloalkyl, cycloalkenyl, or heterocycle;

m is 0, 1, or 2;

and n is 0, 1, or 2.

In certain preferred embodiments, R₁ and R₂ each independently represent a small hydrophobic group, such as a lower alkyl (preferably methyl, ethyl, or propyl, and even more preferably a methyl), a halogen, or a halogenated lower alkyl.

In certain preferred embodiments, R₃ represents a lower alkyl, more preferably methyl, ethyl or propyl, and even more preferably a methyl. In other preferred embodiments, R₃ represents an aryl, such as phenyl or hydroxyphenyl (preferably para-hydroxy). In yet other preferred embodiments, R₃ represents a hydroxyl group. In still other preferred embodiments, R₃ represents —(CH₂)$_m$COOH, and preferably where m is preferably 0 or 1.

In certain preferred embodiments, n is 0.

In certain preferred embodiments of such substrate analogs, the P'₁ is an amino acid analog having a tetrasubstituted Cβ carbon, such as represented in Formula II:

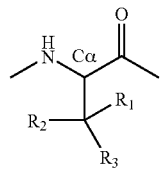

wherein R₁ and R₂ each independently represent a lower alkyl or a halogen; R₃ represents a lower alkyl, an aryl, a hydroxyl group, —(CH₂)$_m$COOH, —(CH₂)$_m$NH₂, —(CH₂)$_m$NC(=NH)NH₂, —(CH₂)$_m$C(=O)NH₂, —SH, or —(CH₂)$_m$SCH₃; and m is 0, 1, or 2.

In certain preferred embodiments, R₁ and R₂ are independently selected from methyl, ethyl, or propyl, and even more preferably a methyl.

In certain preferred embodiments, R₃ represents a lower alkyl, more preferably methyl, ethyl, or propyl, and even more preferably a methyl. In other preferred embodiments, R₃ represents an aryl, such as a phenyl, hydroxyphenyl (preferably para-hydroxy), indole or imidazole. In yet other preferred embodiments, R₃ represents a hydroxyl group. In certain preferred embodiments, R₃ represents —COOH or —CH₂COOH. In still other preferred embodiments, R₃ represents —CH₂CH₂NC(=NH)NH₂, —CH₂C(=O)NH₂, —CH₂CH₂C(=O)NH₂, —SH, or —CH₂SCH₃.

Another aspect of the invention relates to the more general observation that modification of proteinase substrates at the P'₁ residue (of the cleavage site) with an amino acid analog having a tetra-substituted Cβ carbon can markedly increase the in vivo half-life of the resulting analog, e.g., which may have a longer duration of biological action and/or reduced clearance relative to the wild-type polypeptide. Based on this discovery, and its applicability to substrates cleaved by a diverse range of proteinases, the present invention provides a method for producing P'₁ analogs of substrates for such proteinases as serine proteinases, metalloproteinases, aspartic proteinases, and cysteine proteinases.

In certain preferred embodiments, the P'₁ is an amino acid analog having a tetrasubstituted Cβ carbon, such as represented in Formula II:

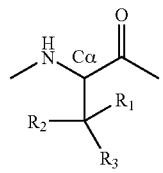

wherein R₁ and R₂ each independently represent a lower alkyl or a halogen; R₃ represents lower alkyl, aryl, hydroxyl group, —(CH₂)$_m$COOH, —(CH₂)$_m$NC(=NH)NH₂, —(CH₂)$_m$C(=O)NH₂, —(CH₂)$_m$NH₂, —SH, —(CH₂)$_m$SCH₃; and m is 0, 1, or 2.

In certain preferred embodiments, R₁ and R₂ each independently represent methyl, ethyl or propyl, and even more preferably methyl.

In certain preferred embodiments, R₃ represents lower alkyl, more preferably methyl, ethyl or propyl, and even more preferably methyl. In other preferred embodiments, R₃ represents an aryl group, such as a phenyl, hydroxyphenyl (preferablyp-hydroxy), indole, or imidazole. In yet other preferred embodiments, $R_3$ represents a hydroxyl group. In certain preferred embodiments, $R_3$ represents —COOH or —CH$_2$COOH. In still other preferred embodiments, $R_3$ represents —CH$_2$CH$_2$NC(=NH)NH$_2$, —CH$_2$C(=O)NH$_2$, —CH$_2$CH$_2$C(=O)NH$_2$, —SH, or —CH$_2$SCH$_3$. For examples of preferred embodiments of modified naturally occurring amino acids, see FIG. 16.

II. Definitions

The term "substrate" refers to a substrate of an enzyme which is catalytically acted on and chemically converted by the enzyme to product(s).

The binding site for a peptide substrate consists of a series of "specificity subsites" across the surface of the enzyme. The term "specificity subsite" refers to a pocket or other site on the enzyme capable of interacting with a portion of a substrate for the enzyme.

In discussing the interactions of peptides and protein substrates with proteinases, e.g., serine and cysteine proteinases and the like, the present application utilizes the nomenclature of Schechter and Berger [(1967) *Biochem. Biophys. Res. Commun.* 27:157-162)]. The individual amino acid residues of a substrate or inhibitor are designated -$P_2$-$P_1$-$P'_1$-$P'_2$-, etc. and the corresponding subsites of the enzyme are designated $S_2$, $S_1$, $S'_1$, $S'_2$, etc. The scissile bond of the substrate is the amide bond linking the $P_1$ and $P'_1$ residues.

A "$P'_1$ residue" refers to the amino acid residue of a substrate polypeptide that becomes the new amino terminus of product polypeptide resulting from proteinase-mediated cleavage of the amide backbone of the substrate polypeptide. To further illustrate, a substrate polypeptide includes an amide backbone bond that is subject to a proteolytic reaction represented by the general scheme:

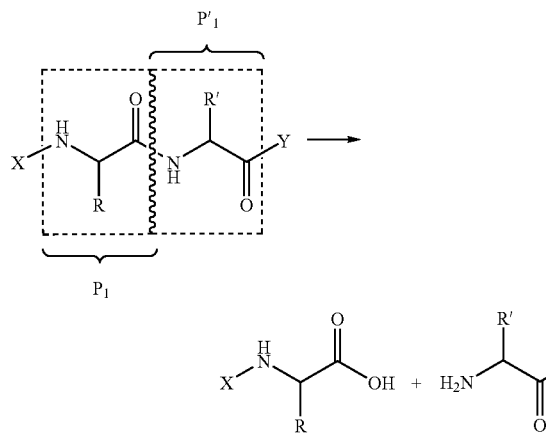

By the term "amino acid residue" is meant an amino acid. In general the abbreviations used herein for designating the naturally occurring amino acids are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group.

The term "amino acid side chain" is that part of an amino acid residue exclusive of the backbone, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH(CH$_3$)—CH$_2$CH$_3$ (the side chain of isoleucine), —CH$_2$CH(CH$_3$)$_2$ (the side chain of leucine) or H-(the side chain of glycine). These side chains are pendant from the backbone Cα carbon.

The term "tetra-substituted Cβ carbon" refers to a carbon atom which is (i) directly pendant from the Cα carbon of the amino acid backbone, and (ii) includes four pendant substituents (including the Cα carbon), none of which is hydrogen.

As used herein, "protein" is a polymer consisting essentially of any of the 20 amino acids. Although "polypeptide" is often used in reference to relatively large proteins, and "peptide" is often used in reference to small protein, usage of these terms in the art overlaps and is varied. Unless evident from the context, the terms "peptide(s)", "protein(s)" and "polypeptide(s)" are used interchangeably herein.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The International Union of Biochemistry and Molecular Biology (1984) has recommended the use of the term "peptidase" for the subset of peptide bond hydrolases (Subclass E.C 3.4.). The widely used term "protease" is synonymous with "peptidase", and they are used interchangeably herein. Peptidases comprise two groups of enzymes: the endopeptidases and the exopeptidases. Endopeptidases cleave peptide bonds at points within a protein, and exopeptidases remove amino acids sequentially from either the N- or C-terminus.

The term "proteinase" is also used as a synonym for endopeptidase. Proteinases are classified according to their catalytic mechanisms. Four mechanistic classes have been recognized by the International Union of Biochemistry and Molecular Biology: serine proteinases, cysteine proteinases, aspartic proteinases, and metalloproteinases.

The class "serine proteinases" comprises two distinct families: the chymotrypsin family which includes the mammalian enzymes such as chymotrypsin, trypsin, elastase or kallikrein, and the substilisin family which includes the bacterial enzymes such as subtilisin. The general three-dimensional structure is different in the two families but they have the same active site geometry and catalysis proceeds via the same mechanism. The serine proteinases exhibit different substrate specificities which are related to amino acid substitutions in the various enzyme subsites (see the nomenclature of Schechter and Berger) interacting with the substrate residues. Three residues which form the catalytic triad are essential in the catalytic process: His-57, Asp-102 and Ser-195 (chymotrypsinogen numbering).

The family of "cysteine proteinases" includes the plant peptidases such as papain, actinidin or bromelain, several mammalian lysosomal cathepsins, the cytosolic calpains (calcium-activated), and several parasitic peptidases (e.g., Trypanosoma, Schistosoma). Papain is the archetype and the best studied member of the family.

Most of the "aspartic proteinases" belong to the pepsin family. The pepsin family includes digestive enzymes such as pepsin and chymosin as well as lysosomal cathepsins D, processing enzymes such as renin, and certain fungal peptidases (penicillopepsin, rhizopuspepsin, endothiapepsin). A second family comprises viral proteinases such as the peptidase from the AIDS virus (HIV) also called retropepsin.

The "metalloproteinases" are found in bacteria, fungi as well as in higher organisms. They differ widely in their sequences and their structures but the great majority of enzymes contain a zinc atom which is catalytically active. Many enzymes contain the sequence HEXXH, which provides two histidine ligands for the zinc whereas the third ligand is either a glutamic acid (thermolysin, neprilysin, alanyl aminopeptidase) or a histidine (astacin).

The term "agonist", as used herein, is meant to refer to a peptide or $P'_1$ analog that retains the bioactivity of the native substrate of interest so as to produce a similar biological effect when administered to an animal.

The term "antagonist" refers to a peptide or $P'_1$ analog that does not retain the bioactivity of the native substrate of interest, or at least at a reduced level of activity relative to the native substrate, and inhibits the biological action of the native substrate.

The term "analog" refers to a molecule substantially similar in function to either the entire receptor molecule or to a fragment thereof.

The term "derivative with minor modifications" with respect to a parent chemical compound, for example an amino acid analog, is used to refer to compounds which are chemically similar to the parent chemical compound. Preferably, a derivative with minor modifications will have minor structural modifications and hence may be considered as "structural analogs" of the original compound.

"Heart-related ailments" includes any chronic or acute pathological event involving the heart and/or associated tissue (e.g., the pericardium, aorta and other associated blood vessels), including ischemia-reperfusion injury; congestive heart failure; cardiac arrest; myocardial infarction; cardiotoxicity caused by compounds such as drugs (e.g., doxorubicin, herceptin, thioridazine and cisapride); cardiac damage due to parasitic infection (bacteria, fimgi, rickettsiae, and viruses, e.g., syphilis, chronic *Trypanosoma cruzi* infection); fulminant cardiac amyloidosis; heart surgery; heart transplantation; traumatic cardiac injury (eg., penetrating or blunt cardiac injury, and aortic valve rapture), surgical repair of a thoracic aortic aneurysm; a suprarenal aortic aneurysm; cardiogenic shock due to myocardial infarction or cardiac failure; neurogenic shock and anaphylaxis.

"Instruction(s)" as used herein means a product label and/or documents describing relevant materials or methodologies pertaining to use of a kit or packaged pharmaceutical. These materials may include any combination of the following: background information, list of components, proposed dosages, warnings regarding possible sideeffects, instructions for administering the drug, technical support, and any other related documents.

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

A "therapeutically effective amount" of a compound, e.g., such as a polypeptide or peptide analog of the present invention, with respect to use in treatment, refers to an amount of the polypeptide or peptide in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "alkyl" refers to a fully saturated branched or unbranched carbon chain radical having the number of carbon atoms specified, or up to 30 carbon atoms if no specification is made. For example, a "lower alkyl" refers to an alkyl having from 1 to 10 carbon atoms, such as methyl, ethyl, propyl, butyl, pentyl, hexyl, heptyl, and octyl, and those which are positional isomers of these alkyls. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6, or 7 carbons in the ring structure.

Moreover, the term "alkyl" (or "lower alkyl") as used throughout the specification, examples, and claims is intended to include both unsubstituted and substituted alky chains, the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, a cyano, a nitro, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxyls, alkylthios, aminoalkyls, carbonyl-substituted alkyls, —$CF_3$, —CN, and the like.

Unless the number of carbons is otherwise specified, "lower alkyl", as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "carbocycle", as used herein, refers to an aromatic or non-aromatic ring in which each atom of the ring is carbon.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloakynyls, aryls and/or heterocyclyls.

"Alkenyl" refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

The term "alkynyl" refers to hydrocarbyl radicals of the scope of alkenyl, but having one or more triple bonds in the radical.

The terms "alkoxyl" or "alkoxy" as used herein refers to an alkyl group, as defined below, having an oxygen radical attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_1$, where m and $R_1$ are described below.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, or the like.

The term "alkylthio" refers to an alkyl group, as defined above, having a sulfur radical attached thereto. In preferred embodiments, the "alkylthio" moiety is represented by one of —(S)-alkyl, —(S)-alkenyl, —(S)-alkynyl, and —(S)—$(CH_2)_m$—$R_1$, wherein m and $R_1$ are defined below. Representative alkylthio groups include methylthio, ethylthio, and the like.

As used herein, the term "nitro" means —$NO_2$; the term "halogen" designates F, Cl, Br or I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formulae:

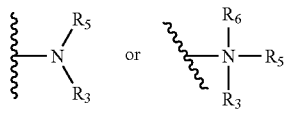

wherein $R_3$, $R_5$ and $R_6$ each independently represent a hydrogen, an alkyl, an alkenyl, —$(CH_2)_m$—$R_1$, or $R_3$ and $R_5$ taken together with the N atom to which they are attached complete a heterocycle having from 4 to 8 atoms in the ring structure; $R_1$ represents an alkenyl, aryl, cycloalkyl, a cycloalkenyl, a heterocyclyl or a polycyclyl; and m is zero or an integer in the range of 1 to 8. In preferred embodiments, only one of $R_3$ or $R_5$ can be a carbonyl, e.g., $R_3$, $R_5$ and the nitrogen together do not form an imide. In even more preferred embodiments, $R_3$ and $R_5$ (and optionally $R_6$) each independently represent a hydrogen, an alkyl, an alkenyl, or —$(CH_2)_m$—$R_1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a $pK_a \geq 7.00$. The protonated forms of these functional groups have $pK_a$s relative to water above 7.00.

The term "carbonyl" is art-recognized and includes such moieties as can be represented by the general formula:

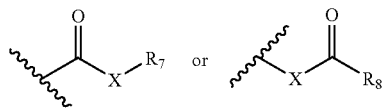

wherein X is a bond or represents an oxygen or a sulfur, and $R_7$ represents a hydrogen, an alkyl, an alkenyl, —$(CH_2)_m$—$R_1$ or a pharmaceutically acceptable salt, $R_8$ represents a hydrogen, an alkyl, an alkenyl or —$(CH_2)_m$—$R_1$, where m and $R_1$ are as defined above. Where X is an oxygen and $R_7$ or $R_8$ is not hydrogen, the formula represents an "ester". Where X is an oxygen, and $R_7$ is as defined above, the moiety is referred to herein as a carboxyl group, and particularly when $R_7$ is a hydrogen, the formula represents a "carboxylic acid". Where X is an oxygen, and $R_8$ is hydrogen, the formula represents a "formate". In general, where the oxygen atom of the above formula is replaced by sulfur, the formula represents a "thiocarbonyl" group. Where X is a sulfur and $R_7$ or $R_8$ is not hydrogen, the formula represents a "thioester" group. Where X is a sulfur and $R_7$ is hydrogen, the formula represents a "thiocarboxylic acid" group. Where X is a sulfur and $R_8$ is hydrogen, the formula represents a "thioformate" group. On the other hand, where X is a bond, and $R_7$ is not hydrogen, the above formula represents a "ketone" group. Where X is a bond, and $R_7$ is hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

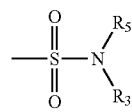

in which $R_3$ and $R_5$ are as defined above.

The term "sulfate" is art recognized and includes a moiety that can be represented by the general formula:

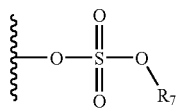

in which $R_7$ is as defined above.

The term "sulfamido" is art recognized and includes a moiety that can be represented by the general formula:

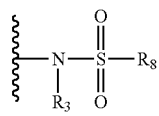

in which $R_2$ and $R_4$ are as defined above.

The term "sulfonate" is art-recognized and includes a moiety that can be represented by the general formula:

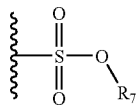

in which $R_7$ is an electron pair, hydrogen, alkyl, cycloalkyl, or aryl.

The terms "sulfoxido" or "sulfinyl", as used herein, refers to a moiety that can be represented by the general formula:

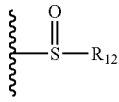

in which $R_{12}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Embodiments (a) $P'_1$ analogs

The present invention provides for the manufacture and use of peptide and $P'_1$ analogs resistant to proteinase-mediated cleavage. Given a native polypeptide typically cleaved by a particular proteinase (e.g., a metalloproteinase, a cysteine proteinase, an aspartic proteinase, or a serine proteinase), one can readily determine the site within the native polypeptide at which the proteinase cleaves (the cleavage site). Once the cleavage site is identified, $P'_1$ analogs can be readily made according to the methods of the present invention. Given the depth of understanding in the art of enzymology, the preferred cleavage sites of a large number of proteinases are known, and the identification of the consensus cleavage site in a given native polypeptide can be rapidly and easily accomplished by simply examining the amino acid sequence.

In the event that the cleavage site within a particular polypeptide is not known or can not be rapidly determined by simply examining the amino acid sequence, the cleavage site can be determined by simply incubating native polypeptide and proteinase to allow cleavage, separating the cleaved polypeptide species (e.g., by electrophoresis), and sequencing the cleaved peptide fragments. By determining the sequence of the ends of the cleaved peptide fragment, and comparing this sequence to that of the full-length polypeptide sequence, one can rapidly and easily identify or verify the cleavage site within a native polypeptide at which a proteinase acts.

Another exemplary method for rapidly determining the substrate specificity of a proteinase is provided, for example, by PCT Publication WO0061789.

The present invention provides generalizable methods for constructing proteinase resistant $P'_1$ analogs. The present invention contemplates the design and use of $P'_1$ analogs resistant to metalloproteinases, cysteine proteinases, aspartic proteinases, and serine proteinases. For instant, the subject analogs can be rendered resistant to cleavage by proteinases selected from: an aminopeptidase (EC 3.4.11.-), a dipeptidase (EC 3.4.13.-), a dipeptidyl-peptidase or tripeptidyl peptidase (EC 3.4.14.-), a peptidyl-dipeptidase (EC 3.4.15.-), a serine-type carboxypeptidase (EC 3.4.16.-), a metallocarboxypeptidase (EC 3.4.17.-), a cysteine-type carboxypeptidase (EC 3.4.18.-), an omegapeptidase (EC 3.4.19.-), a serine proteinase (EC 3.4.21.-), a cysteine proteinase (EC 3.4.22.-), an aspartic proteinase (EC 3.4.23.-), a metallo proteinase (EC 3.4.24.-), or a proteinase of unknown mechanism (EC 3.4.99.-). The EC designation following each class of proteinase is that used in the recommendation of the International Union of Biochemistry and Molecular Biology (1984), and these subclass headings are provided here for reference.

To further illustrate the exemplary proteinases for which proteinase-resistant $P'_1$ analogs are contemplated, an non-exhaustive list of proteinases include: leucyl aminopeptidase, membrane alanine aminopeptidase, cystinyl aminopeptidase, tripeptide aminopeptidase, prolyl aminopeptidase, aminopeptidase B, glutamyl aminopeptidase, Xaa-Pro aminopeptidase, bacterial leucyl aminopeptidase, clostridial aminopeptidase, cytosol alanyl aminopeptidase, lysyl aminopeptidase, Xaa-Trp aminopeptidase, tryptophanyl aminopeptidase, methionyl aninopeptidase, D-stereospecific aninopeptidase, aminopeptidase Ey, vacuolar aminopeptidase I, Xaa-His dipeptidase, Xaa-Arg dipeptidase, Xaa-methyl-His dipeptidase, Cys-Gly dipeptidase, Glu-Glu dipeptidase, Pro-Xaa dipeptidase, Xaa-Pro dipeptidase, Met-Xaa dipeptidase, non-stereospecific dipeptidase, cytosol non-specific dipeptidase, membrane dipeptidase, Beta-Ala-His dipeptidase, Dipeptidyl-peptidase I (DPP I), Dipeptidyl-peptidase II (DPP II), Dipeptidyl-peptidase III (DPP III), Dipeptidyl-peptidase IV(DPP IV), Dipeptidyl-dipeptidase, Tripeptidyl-peptidase I, Tripeptidyl-peptidase II, Xaa-Pro dipeptidyl-peptidase, peptidyl-dipeptidase A, peptidyl-dipeptidase B, peptidyl-dipeptidase Dcp, lysosomal Pro-X carboxypeptidase, Serine-type D-Ala-D-Ala carboxypeptidase, carboxypeptidase C, carboxypeptidase D, carboxypeptidase A, carboxypeptidase B, lysine(arginine) carboxypeptidase, Gly-X carboxypeptidase, alanine carboxypeptidase, muramoylpentapeptide carboxypeptidase, carboxypeptidase H, glutamate carboxypeptidase, carboxypeptidase M, muramoyltetrapeptide carboxypeptidase, zinc D-Ala-D-Ala carboxypeptidase, carboxypeptidase A2, membrane Pro-X carboxypeptidase, tubulinyl-Tyr carboxypeptidase, carboxypeptidase T, thermostable carboxypeptidase 1, carboxypeptidase U, glutamate carboxypeptidase II, metallocarboxypeptidase D, cysteine-type carboxypeptidase, acylaminoacyl-peptidase, peptidyl-glycinamidase, pyroglutamyl-peptidase I, beta-aspartyl-peptidase, pyroglutamyl-peptidase II, N-formylmethionyl-peptidase, pteroylpoly-gamma-glutamate carboxypeptidase, gamma-glutamyl hydrolase, gamma-D-glutamyl-meso-diaminopimelate peptidase I, chymotrypsin, chymotrypsin C, metridin, trypsin, thrombin, coagulation factor Xa, plasmin, enteropeptidase, acrosin, alpha-lytic endopeptidase, glutamyl endopeptidase, cathepsin G, coagulation factor VIIa, coagulation factor Ixa, cucumisin, prolyl oligopeptidase, coagulation factor XIa, brachyurin, plasma kallikrein, tissue kallikrein, pancreatic elastase, leukocyte elastase, coagulation factor XIIa, chymase, complement component C1r, complement component C1s, classical-complement pathway C3/C5 convertase, complement factor I, complement factor D, alternative-complement pathway C3/C5 convertase, cerevisin, hypodermin C, lysyl endopeptidase, endopeptidase La, gamma-renin, venombin AB, leucyl endopeptidase, tryptase, scutelarin, kexin, subtilisin, oryzin, proteinase K, thermomycolin, thermitase, endopeptidase So, T-plasminogen activator, protein C (activated), pancreatic endopeptidase E, pancreatic elastase II, IgA-specific serine endopeptidase, U-plasminogen activator, venombin A, furin, myeloblastin, semenogelase, granzyme A, granzyme B, streptogrisin A, streptogrisin B, glutamyl endopeptidase II, oligopeptidase B, limulus clotting factor C, limulus clotting factor B, limulus clotting enzyme, omptin, repressor lexA, signal peptidase I, togavirin, flavirin, endopeptidase Clp, proprotein convertase 1, proprotein convertase 2, snake venom factor V activator, lactocepin, cathepsin B, papain, ficain, chymopapain, asclepain, clostripain, streptopain, actinidain, cathepsin L, cathepsin H, calpain, cathepsin T, glycyl endopeptidase, cancer procoagulant, cathepsin S, picomain 3C, picornain 2A, caricain, ananain, stem bromelain, fruit bromelain, legumain, histolysain, caspase-1, gingipain R, cathepsin K, pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin A, scytalidopepsin B, xanthomonapepsin, cathepsin E, barrierpepsin, signal peptidase II, pseudomonapepsin, plasmepsin I, plasmepsin II, phytepsin, atrolysin A, microbial collagenase, leucolysin, interstitial collagenase, neprilysin, envelysin, IgA-specific metalloendopeptidase, procollagen N-endopeptidase, thimet oligopeptidase, neurolysin, stromelysin 1, meprin A, procollagen C-endopeptidase, peptidyl-Lys metalloendopeptidase, astacin, stromelysin 2, matrilysin, gelatinase A, aeromonolysin, pseudolysin, thermolysin, bacillolysin, aureolysin, coccolysin, mycolysin, beta-lytic metalloendopeptidase, peptidyl-Asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-sialoglycoprotein endopeptidase, russellysin, mitochondrial intermediate peptidase, dactylysin, nardilysin, magnolysin, meprin B, mitochondrial processing peptidase, macrophage elastase, choriolysin L, choriolysin H, tentoxilysin, bontoxilysin, oligopeptidase A, endothelin-converting enzyme 1, fibrolase, jararhagin, fragilysin, and multicatalytic endopeptidase complex.

One aspect of the present invention is a polypeptide sequence encoding for a proteinase-resistant analog of a polypeptide hormone that has an N-terminal sequence selected from NH$_2$-Xaa-Ala-Yaa- and NH$_2$-Xaa-Pro-Yaa-, where Xaa and Yaa each independently represent an amino acid residue. In certain embodiments, Xaa is an amino acid with aromatic side chain. In certain embodiments, Xaa is selected from histidine, tyrosine, tryptophan, and phenylalanine. In certain embodiments, Yaa is an amino acid residue with an acidic side chain. In certain embodiments, Yaa, is selected from aspartic acid and glutamic acid.

By way of example, in certain embodiments, the proteinase is a serine proteinase. In some embodiment the proteinase is a dipeptidyl peptidase. An exemplary dipeptidyl peptidase is dipeptidyl peptidase IV (DPP IV). DPP IV activity alters the biological activity of a large number of bioactive proteins and polypeptides. In addition to the potential DPP IV substrates disclosed in U.S. Pat. No. 6,090,786, the present invention is also directed to analogs of GLP-1, GLP-2, and GIP. In certain embodiments, the peptide hormone is a naturally occurring variety found in mammals. In certain embodiments, the peptide hormone is a naturally, or artificially mutated variety of a naturally occurring (wild type) peptide hormone. Thus, natural and synthetic peptide hormones are within the scope of peptide hormones contemplated for the modifications. Thus in certain embodiments, the present invention provides DPP IV proteolysis-resistant analogs of the aforementioned peptide hormones.

To provide further illustration of proteinase-resistant P'$_1$ analogs, Table I provides a list of several human hormones that are substrates of DPP IV The P'$_1$ amino acid in each peptide hormone is labeled with an asterisk. Exemplary analogs are shown, wherein X is an amino acid analog having a sidechain represented in, for example, Formula II above. One can readily construct a similar table comprising substrates for other serine proteinases and readily identify the P'$_1$ amino acid. Similarly, one can readily construct a table comprising substrates for a given aspartic proteinase, cysteine proteinase, or metalloproteinase and identify the P'$_1$ amino acid.

In certain preferred embodiments of the exendin-4 analogs, X is an amino acid analog of Formula (II). In preferred embodiments, X is an amino acid analog of Formula (II)

TABLE 1

Exemplary analogs of DPP IV substrates

| | Native sequence | Exemplary Analog |
|---|---|---|
| Human glucagon-like peptide GLP-1 (7-37) | HAE*GTFTSDVSSYLEGQ AAKEFIAWLVKGRG (SEQ ID NO: 1) | HAXGTFTSDVSSYLEGQA AKEFIAWLVKGRG (SEQ ID NO: 10) |
| Human glucagon-like peptide 1: GLP-1 (7-36)NH$_2$ | HAE*GTFTSDVSSYLEGQ AAKEFIAWLVKGR-NH$_2$ (SEQ ID NO: 2) | HAXGTFTSDVSSYLEGQA AKEFIAWLVKGR-NH$_2$ (SEQ ID NO: 11) |
| Human glucagon-like peptide 2, GLP-2 | HAD*GSFSDEMNTILDNL AARDFINWLIQTKITD (SEQ ID NO: 3) | HAXGSFSDEMNTILDNLA ARDFINWLIQTKITD (SEQ ID NO: 12) |
| Human glucose-dependent insulinotropic polypeptide, GIP | YAE*GTFISDYSIAMDKI HQQDFVNWLLAQKGKKNDWKH NITQ (SEQ ID NO: 4) | YAXGTFISDYSIAMDKIHQ QDFVNWLLAQKGKKNDWKHNIT Q (SEQ ID NO: 13) |
| Human neuropeptide Y, NPY | YPS*KPDNPGEDAPAED MARYYSALRHYINLITRQRY (SEQ ID NO: 5) | YPXKPDNPGEDAPAEDM ARYYSALRHYINLITRQRY (SEQ ID NO: 14) |
| Human pancreatic polypeptide PP | APL*EPVYPGDNATPEQ MAQYAADLRRY (SEQ ID NO: 6) | APXEPVYPGDNATPEQMA QYAADLRRY (SEQ ID NO: 15) |
| Human peptide YY | YPI*KPEAPGEDASPEEL NRYYASLRHYLNLVTRQRY (SEQ ID NO: 7) | YPXKPEAPGEDASPEELN RYYASLRHYLNLVTRQRY (SEQ ID NO: 16) |
| exendin-4 (GLP-1 analog) | HGE*GTFTSDLSKEMEEE AVRLFIEWLKNGGPSSGAPPPS-NH$_2$ (SEQ ID NO: 8) | HGXGTFTSDLSKEMEEEA VRLFIEWLKNGGPSSGAPPPS-NH$_2$ (SEQ ID NO: 17) |
| exendin-3 (GLP-1 analog) | HSD*GTFTSDLSKQMEEE AVRLFIEWLKNGGPSSGAPPPS (SEQ ID NO: 9) | HSXGTFTSDLSKQMEEEA VRLFIEWLKNGGPSSGAPPPS (SEQ ID NO: 18) |

In certain embodiments of the GLP-1(7-37), GLP-1(7-36)NH$_2$, GLP-1 (7-36)-Exendin tail-NH$_2$, GLP-2, GIP and exendin-3 analogs, X is an amino acid analog of Formula (II). In preferred embodiments, X is an amino acid analog of Formula (II) wherein $R_1$ and $R_2$ each independently represent methyl, ethyl, or propyl. In the most preferred embodiment, X is an amino acid analog of Formula (II), wherein both $R_1$ and $R_2$ are methyl, and $R_3$ is selected from —COOH and —CH$_2$—COOH.

In certain preferred embodiments of the NPY analogs, X is an amino acid analog of Formula (II). In preferred embodiments, X is an amino acid analog of Formula (II) wherein $R_1$ and $R_2$ each independently represent methyl, ethyl, or propyl. In the most preferred embodiment, X is an amino acid analog of Formula (II), wherein both $R_1$ and $R_2$ are methyl, and $R_3$ represents —OH.

In certain preferred embodiments of the pancreatic polypeptide PP and peptide YY (PYY) analogs, X is an amino acid analog of Formula (II). In preferred embodiments, X is an amino acid analog of Formula (II) wherein $R_1$, $R_2$, and $R_3$ each independently represent methyl, ethyl, or propyl. In the most preferred embodiment, X is an amino acid analog of Formula (II), wherein both $R_1$ and $R_2$ are methyl, and $R_3$ represents —CH(CH$_3$)$_2$ or —CH$_2$—CH$_3$.

wherein $R_1$ and $R_2$ each independently represent methyl, ethyl, or propyl, and $R_3$ represents —(CH$_2$)$_m$—C(=O)NH$_2$ (wherein m is 0, 1, or 2). In the most preferred embodiment, X is an amino acid analog of Formula (II), wherein both $R_1$ and $R_2$ are methyl, and $R_3$ represents —CH$_2$—C(=O)NH$_2$.

More generally, the present invention specifically contemplates the generation of analogs for peptide and polypeptide factors that have an amino acid sequence Xaa-Ala-Yaa-R or Xaa-Pro-Yaa-R' wherein Xaa and Yaa represent amino acid residues, and R and R', independently for each occurrence, represent polypeptide chains comprising 1 to about 100 amino acid residues and wherein in the analog sequence Yaa is replaced by an amino acid residue represented by Formula I or Formula II. The invention further contemplates the modification of variant polypeptides that differ in sequence from the wildtype polypeptide in order to produce variant P'$_1$ analogs. Such variants are at least 80%, 85%, 90%, 95%, 97%, 99%, or greater than 99% identical to the wildtype polypeptide.

In certain embodiments, R is a polypeptide having an amino acid sequence selected from the group consisting of

```
GTFTSDVSSYLEGQAAKEFIAWLVKGR,            (SEQ ID NO: 19)

(SEQ ID NO: 20)
GTFTSDVSSYLEGQAAKEFIAWLVKGRPSSGAPPPS-NH2,

GTFTSDVSSYLEGQAAKEFIAWLVKGR-NH2,        (SEQ ID NO: 21)

GSFSDEMNTILDNLAARDFINWLIQTKITD,         (SEQ ID NO: 22)

and (SEQ ID NO: 23)
GTFISDYSIAMDKIHQQDFVNWLLAQKGKKNDWKHNITQ,
``` or a sequence that differs by 5 or fewer amino acid residues thereto, even more preferably differs by no more than 4, 3, or even 2 amino acid residues.

In certain embodiments, R is a polypeptide having an amino acid sequence selected from the group consisting of

```
KPDNPGEDAPAEDMARYYSALRHYINLITRQRY,      (SEQ ID NO: 24)

EPVYPGDNATPEQMAQYAADLRRY,               (SEQ ID NO: 25)

and

KPEAPGEDASPEELNRYYASLRHYLNLVTRQRY,      (SEQ ID NO: 26)
``` or a sequence that differs by 5 or fewer amino acid residues thereto, even more preferably differs by no more than 4, 3, or even 2 amino acid residues.

Proteinase-resistant GHRH analogs provide still further illustration of the generalizable methods and compositions of the present invention. Regulated expression of the growth hormone (GH) pathway is essential for optimal linear growth, as well as for homeostasis of carbohydrate, protein, and fat metabolism. Growth hormone synthesis and its pulsatile secretion from the anterior pituitary is stimulated by growth hormone-releasing hormone (GHRH) and inhibited by somatostatin, both hypothalamic hormones. Growth hormone increases production of insulin-like growth factor-I (IGF-I) primarily in the liver, as well as other target organs.

Linear growth velocity and body composition respond to GH or GHRH replacement therapies in a broad spectrum of conditions, both in humans and in farm animals. The etiology of these conditions can vary significantly. In 50% of human GH deficiencies the GHRH-GH-IGF-I axis is functionally intact but does not elicit the appropriate biological responses in its target tissues. Similar phenotypes are produced by genetic defects at different points in the GH axis, as well as in non-GH-deficient short stature. In several conditions characterized by growth retardation in which the GHRH-GH-IGF-I axis is functional, such as Turner's syndrome, hypochondroplasia, Crohn's disease, intrauterine growth retardation, or chronic renal insufficiency, therapeutic administration of GHRH or GH has been shown to be effective in promoting growth.

In the elderly, there is considerable decrement in the activity of the GHRH-GH-IGF-I axis that results in reduced GH secretion and IGF-I production. These changes are associated with a loss of skeletal muscle mass (sarcopenia), osteoporosis, increased fat deposition, and decreased lean body mass. It has been demonstrated that the development of these changes can be offset by recombinant GH therapy.

Current GH therapy has several shortcomings, however, including frequent subcutaneous or intravenous injections, insulin resistance, and impaired glucose tolerance. Children treated with GH are vulnerable also to premature epiphyseal closure and slippage of the capital femoral epiphysis. In domestic livestock, GHRH and GH stimulate milk production, increase feed-to-milk conversion, and sustain growth, primarily by increasing lean body mass, and increase overall feed efficiency. Hot and chilled carcass weights are increased, and carcass lipid (percentage of soft-tissue mass) is decreased by GHRH.

Although GHRH protein therapy entrains and stimulates normal cyclical GH secretion with virtually no side effects, the short half-life of the molecule in vivo requires frequent (one to three times per day) intravenous, subcutaneous, or intranasal (at a 300-fold higher dose) administrations. Thus, recombinant GHRH administration is not practical as a chronic therapy.

GHRH has a primary sequence as indicated below. The $P'_1$ amino acid (in this case as aspartic acid) is marked by an asterisk and bolded.

```
                                        (SEQ ID NO: 27)
YAD*AIFTNSYRKVLGQLSARKLLQDIMSRQQGESNQERGARARL
```

GHRH is cleaved by the post-proline cleaving enzyme prolyl endopeptidase (PEP). PEP is a cytosolic endopeptidase which cleaves a variety of substrates in addition to GHRH including neuroactive peptides, such as arginine vasopressin, luteinizing hormone-releasing hormone, thyrotropin releasing hormone, alpha-melanocyte secreting hormone, substance P, oxytocin, bradykinin, neurotensin and angiotensin (Ag) I and II.

Accordingly, in certain embodiment, the invention contemplates GHRH analogs having an amino acid sequence represented in the general formula:

Tyr-Ala-Yaa-R wherein Yaa represent amino acid having a sidechain represented in Formula I or Formula II above, and R represents a polypeptide chain having the sequence AIFT-NSYRKVLGQLSARKLLQDIMSRQQGESN-QERGARARL (SEQ ID NO: 28) or a sequence that differs by 5 or fewer amino acid residues thereto, even more preferably differs by no more than 4, 3, or even 2 amino acid residues. In certain preferred embodiments, $R_1$ and $R_2$ each independently represent a methyl, ethyl or propyl, and even more preferably a methyl, and $R_3$ represents —COOH or —CH$_2$COOH.

To provide an additional example still, two of the primary sites of actions for angiotensin (ANG)-(1—7) are the vasculature and the kidney. ANG-(1—7) is hydrolyzed primarily to ANG-(1—5) by pulmonary membranes. The ANG-converting enzyme (ACE) inhibitor lisinopril abolished the generation of ANG-(1—5), as well as that of smaller metabolites. Accordingly, a class of (ANG)-(1—7) peptide analogs resistant to cleavage could have the same or similar effect as ACE inhibitor. In other words, such peptide analogs would increase the effective concentration and/or half-life of (ANG)-(1—7).

Yet another example with important applications to the generation of therapeutic agents for the treatment of disease is IGFBP-3. IGFBP-3 in serum and other body fluids is cleaved by proteinases, and the proteolytic products have greatly reduced or no affinity for IGF's. Increased proteolysis of IGFBP-3 has been observed in various clinical and physiological conditions including both pregnancy and certain cancers. Accordingly, the design of proteinase resistant IGFBP-3 analogs may be particularly useful in maintaining appropriate IGFBP-3 levels, for example in cancers associated with increased proteolysis of IGFBP-3.

The above cited examples are meant solely for illustration. The present invention provides a generalizable method by which virtually any polypeptide that is a substrate for a proteinase can be manipulated with a tetra-substitution at the cleavage site to produce a proteinase resistant $P'_1$ analog. Exemplary polypeptides that are substrates for proteinases and accordingly which can be manipulated at the cleavage site to produce a proteinase resistant $P'_1$ analog include, without limitation, enkephalin, Leu-enkephalin, Met-enkephalin, angiotensin I, angiotensin II, vasopressin, endothelin, vasoactive intestinal peptide, neurotensin, endorphins, insulin, gramicidin, paracelsin, delta-sleep inducing peptide, gonadotropin-releasing hormone, human parathyroid hormone (1-34), truncated erythropoietin analogues described in Wrighton et al., 1996, Science 273:458-463), specifically EMP-1, Atrial natriuretic peptide (ANP, ANF), human brain natriuretic peptide (hBNP), cecropin, kinetensin, neurophysins, elafin, guamerin, atriopeptin I, atriopeptin II, atriopeptin III, deltorphin I, deltorphin II, vasotocin, bradykinin, dynorphin, dynorphin A, dynorphin B, growth hormone release factor, growth hormone, growth hormone releasing peptide, oxytocin, calcitonin, calcitonin gene-related peptide, calcitonin gene-related peptide II, growth hormone releasing peptide, tachykinin, adrenocorticotropic hormone (ACTH), brain natriuretic polypeptide, cholecystokinin, corticotropin releasing factor, diazeparn binding inhibitor fragment, FMRF-amide, galanin, gastric releasing polypeptide, gastric inhibitory polypeptide, gastrin, gastrin releasing peptide, glucagon, glucagon-like peptide-1, glucagon-like peptide-2, LHRH, melanin concentrating hormone, melanocyte stimulating hormone (MSH), alpha-MSH, morphine modulating peptides, motilin, neurokinin A, neurokinin B, neuromedin 13, neuromedin C, neuromedin K, neuromedin N, neuromedin U, neuropeptide K, neuropeptide Y, pituitary adenylate cyclase activating polypeptide (PACAP), pancreatic polypeptide, peptide YY, peptide histidine-methionine amide (PHM), secretin, somatostatin, substance K, thyrotropin-releasing hormone (TRH), kyotorphin, melanostatin (MIF-1), thrombopoeitin analogs, in particular AF 12505, insulin-like growth factor I (57-70), insulin-like growth factor I (30-41), insulin-like growth factor I (24-41), insulin-like growth factor II (33-40), insulin-like growth factor II (33-40), insulin-like growth factor II (69-84), growth hormone (GH)-releasing peptide-6 (GHRP-6), β-Interleukin 1 (163-171), β-Interleukin II (44-56), Interleukin II (60-70), epidermal growth factor, bivalirudin (Hirulog), hirulog-I, C-type natriuretic peptide, ornipressin (also known as 8-omithine-vasopressin), octreotide, eptifibatide, calcitonin gene-related peptide (CGRP), endomorphin-1; endomorphin-2, nociceptin, angiotensinogen, adrenomodullin, antiarrhytmic peptide (AA-P), Antagonist G, indolicidin, osteocalcin, cortistatin 29, cortistatin 14, PD-145065, PD-142893, fibrinogen binding inhibitor peptide, leptin, GR 83074, parathyroid hormone related peptide, angiotensinogen, leupeptin, and any modified or truncated analog thereof.

In many embodiments, the analog will be selected to retain one or more of the in vitro or in vivo activity of the native substrate. The in vitro and in vivo activities may be measured using any protocol available to one of ordinary skill that are appropriate for the particular polypeptide. Exemplary functional activities that can be measured to ascertain whether a $P'_1$ analog maintains the same or similar functional activity include ability of the polypeptide to bind its receptor(s) in a cell based or cell free assay, ability of the polypeptide to induce a change (e.g., proliferation, differentiation, survival, growth, migration, etc) in a cell responsive to the polypeptide, ability of the polypeptide to modulate the expression of one or more other genes or proteins in a cell responsive to the polypeptide.

In certain embodiments, the analog has substantially similar activitiy as the native polypeptide (e.g., about 80%, 90%, 100%, 110%, or 120% as active as the native polypeptide). In some embodiment, the analog is less active than the native polypeptide (e.g., about 50%, 60%, 70%, or 75% as active as the native polypeptide). We note that an analog that is somewhat less active may be useful, such as in vivo or in cell culture, if the decrease in activity still provides the ability to provide a sufficient local concentration of analog for a sufficient period of time. Thus, an increase in half-life obtained by proteinase resistance may off-set the decrease in activity caused by the construction of the analog. In still other embodiment, the analog is more active that the native polypeptide (e.g., about 130%, 150%, 175%, 200%, 300%, 500%, 800%, or even 1000% as active as the native polypeptide). In any of the foregoing, by "activitiy" is meant one or more functions of the native polypeptide. For example, an activity (e.g., a biological fuiction) of a polypeptide may be receptor binding, cofactor interaction, ability to bind to DNA, ability to act as a transcriptional activator or repressor, the ability to participate in a particular signal transduction pathway, and the ability to influence cell behavior (e.g., proliferation, differentiation, survival, or migration).

Such activites may be expressed, for example, as relative binding constants (such as for receptor binding), effective concentrations ($EC_{50}$) and/or effective doses ($ED_{50}$).

Exemplary $P'_1$ analogs have an increased half life incomparison to the native polypeptide (in vitro and/or in vivo) due to the resistance of the $P'_1$ analogs to a proteinase which typically cleaves the native polypeptide. However, it will be generally appreciated that various $P'_1$ analogs will have different half-lives (as well as a different change in half-life in comparison to the native polypeptide). The in vitro and/or in vivo half-life can be readily measured by one of skill in the art using standard methods. In certain embodiments, the analog has an in vitro or in vivo half life that is about a factor of 0.5, 0.6, 0.7, 0.8., 0.9, 1.0, 1.3, 1.5, 2, 3, 5, 10, 25, 30, 50, 75, 100, or even greater than 100 times the in vitro and/or in vivo half-life of the native polypeptide under similar half-life measurement assay conditions.

(b) Synthesis of Peptide Hormone Analogs

The peptides of the invention can be prepared by standard solid phase synthesis. See, e.g., Stewart, J. M., et al., Solid Phase Synthesis (Pierce Chemical Co., 2d ed. 1984).

The analogs of the invention can be prepared using standard solid-phase techniques for the synthesis of peptides. As is generally known, peptides of the requisite length can be prepared using commercially available equipment and reagents following the manufacturers' instructions for blocking interfering groups, protecting the amino acid to be reacted, coupling, deprotection, and capping of unreacted residues. Suitable equipment can be obtained, for example, from Applied BioSystems in Foster City, Calif., or Biosearch Corporation in San Raphael, Calif.

In a preferred method, the peptides are synthesized using standard automated solid-phase synthesis protocols employing t-butoxycarbonyl-alpha-amino acids with appropriate side-chain protection. Completed peptide is removed from the solid phase support with simultaneous side-chain deprotection using the standard hydrogen fluoride method. Crude peptides are further purified by semi-preparative reverse phase-HPLC (Vydac $C_{18}$) using acetonitrile gradients in 0.1% trifluoroacetic acid (TFA). The peptides are vacuum dried to remove acetonitrile and lyophilized from a solution of 0.1% TFA in water. Purity is verified by analytical RP-HPLC. The peptides can be lyophilized and then solubilized in either water or 0.01M acetic acid at concentrations of 1-2 mg/mL by weight.

The use of the aforementioned synthetic methods is needed if nonencoded amino acids or the D-forms of amino acids occur in the peptides. However, for peptides which are gene-encoded, recourse can also be had to recombinant techniques using readily synthesized DNA sequences in commercially available expression systems.

Accordingly, one aspect of the present invention is a method of preparing an analog of a polypeptide, wherein said peptide is resistant to a proteinase selected from the group consisting of a metalloproteinase, a serine proteinase, an aspartic proteinase, and a cysteine proteinase. In one embodiment, the analog is resistant to a serine proteinase. In another embodiment, the serine proteinase is a dipeptidyl peptidase such as a post-proline cleaving dipeptidyl peptidase. In yet another embodiment, the post-proline cleaving dipeptidyl peptidase is DPP IV. In any of the foregoing, preparation of the proteinase resistant peptide analog may comprise substituting one or more amino acid residues in the peptide hormone with an amino acid residue represented by Formula I or Formula II shown above.

Another aspect of the present invention is a method for preparing an analog of a peptide hormone, wherein the peptide hormone has an N-terminal amino acid sequence Xaa-Ala-Yaa-R, or Xaa-Pro-Yaa-R', wherein Xaa and Yaa represent amino acid residues and R and R', independently for each occurrence, represent polypeptide chains comprising 1 to about 100 amino acid residues (preferably about <90, <80, <70, <60, <50, <40, <30, <20, or even <10 amino acid residues) and wherein in the analog sequence Yaa is replaced by an amino acid residue represented by Formula I or Formula II shown above.

(c) Functional Assays

As outlined in detail herein, the present invention provides a generalizable way to make proteinase resistant $P'_1$ analogs. Based on knowledge of the cleavage site for a particular enzyme in a given substrate, and based on the guidance provided herein for constructing proteinase resistant analogs, a number of $P'_1$ analogs resistant to cleavage by, for example, serine proteinases, metalloproteinases, aspartic proteinases, and cysteine proteinases, can be readily constructed. Once candidate $P'_1$ analogs have been made, the activity of the $P'_1$ analog (e.g., the suitability of the candidate analog as a proteinase substrate) can be readily measured and compared to that of the native polypeptide.

A variety of methods for assessing whether a candidate $P'_1$ analog is resistant to proteolysis are available in the art. For example, the ability of a particular proteinase to cleave a $P'_1$ analog can be measured in a cell free system in vitro. In one such embodiment of a cell free assay system, candidate substrate (e.g., $P'_1$ analog and/or native polypeptide) is end labeled with a detectable label such as radioactivity. Labelled substrate is incubated in the presence of proteinase. Over time, samples of the reaction mixture can be stopped and run on a gel. A shift in the size of the radioactive band indicates that the polypeptide is cleaved by the proteinase, and the rate at which this shift occurs indicates the rate at which the polypeptide is cleaved by the proteinase. This rate can be compared to that observed with the native polypeptide.

To further illustrate, an exemplary experiment to test a particular $P'_1$ analog might involve the following. The native polypeptide and the putative $P'_1$ analog are each radioactively labelled (note: for the purposes of labeling, all that is necessary is that cleavage of the polypeptide produces a radioactive fragment which differs in size from the full length labeled polypeptide). The labeled native polypeptide and $P'_1$ analog are incubated with the particular proteinase. Following incubation, both native polypeptide and $P'_1$ analog are separated by gel electrophoresis, and the migration of the labeled species is examined. Since the particular proteinase is known to cleave the native polypeptide, one would expect to see a shift in the size of the labeled fragment of the native polypeptide (before and after incubation with enzyme) with the smaller fragment corresponding to a cleavage product. However, if the $P'_1$ analog is resistant to proteolysis, this shift in mobility following incubation with proteinase will either not occur, or will occur much more slowly than occurs for the proteolysis of the native protein.

The relative ability of a proteinase to cleave a $P'_1$ analog in comparison to a native polypeptide can also be assessed in a cell based in vitro system. In one such cell based assay, a cell which expresses a given proteinase is contacted with a native polypeptide or a $P'_1$ analog such that the native polypeptide or $P'_1$ analog is expressed in the cell. Much like in the cell free assay described above, the native polypeptide and $P'_1$ analog are detectably labelled. Cleavage of the native polypeptide and the $P'_1$ analog can be measured and compared by extracting protein from the cells and measuring the migration of labeled protein.

In a further example of a cell based assay, a cell which does not express a given proteinase is contacted with a detectably labeled native polypeptide or $P'_1$ analog such that the native polypeptide or $P'_1$ analog is expressed in the cell. The cell is further contacted with the particular proteinase such that the proteinase is expressed in the cell. Cleavage of the native polypeptide and the $P'_1$ analog can be measured and compared by extracting protein from the cells and measuring the migration of labeled protein.

In any of the aforementioned cell based assays, the invention contemplates the use of any of a number of primary cells or cell lines. In some instances, it may be advantageous to select a particular cell or cell line in which to conduct in vitro analysis. For example, it may be advantageous in some instances to select a cell line that is more closely related to the cell type in which one eventually wishes to use the $P'_1$ analog. However, in other instances, it may be most useful to perform initial screening and testing of candidate $P'_1$ analogs in a possibly unrelated cell type or cell line selected primarily based on convenience, and perform later safety and efficacy testing in more specific cell lines or in animal models as needed.

In addition to cell free and cell-based assays, the proteinase resistance of a particular $P'_1$ analog can be measured in vivo using any of a number of animal models. Initial testing of the proteolysis of a given $P'_1$ analog can be assessed in wildtype animals. During such initial testing, the potential positive or negative effects of the $P'_1$ analog are not the question, but rather the question is whether a particular $P'_1$ analog is resistant to proteolysis. Once a particular $P'_1$ analog is shown to be resistant to proteolysis using any of the cell free, cell based, or in vivo assays described above, further in vitro and in vivo testing of the $P'_1$ analog can be conducted to ascertain the therapeutic effectiveness of the $P'_1$ analog.

Additional assays can be used to evaluate the specific functional activity of a proteinase resistant $P'_1$ analog. Such assays can be selected based on the particular $P'_1$ analog. For example, when the polypeptide is a growth factor, the functional activity of the growth factor analog can be assessed by measuring the ability of the growth factor to bind its growth factor receptor in a cell free or cell based assay, and comparing this to the ability of the native growth factor. When the polypeptide is a peptide hormone, the functional activity of the peptide hormone analog can be assessed by measuring the ability of the peptide hormone analog to bind its receptor in a cell free or cell based assay, and comparing this to the ability of the native peptide hormone. When the polypeptide is a transcription factor, the functional activity of the transcription factor analog can be assessed by measuring the ability to bind to an appropriate DNA consensus sequence or the ability to activate a reporter construct containing an appropriate consensus sequence, and comparing this ability to that of the native transcription factor. In any of these examples, functional activity can also be measured in animal models.

The following illustrative example provides potential methods of assessing a functional activity of analogs of a particular polypeptide.

1. Assays of Insulinotropic Activity

In certain embodiments, the $P'_1$ analogs of the present invention are peptide hormone analogs. Active GLP-1 peptides, 7-34, 7-35, 7-36, and 7-37, have insulinotorpic activity, and the invention provides methods for making peptide analogs of these active GLP-1 peptides. The resistance of GLP-1 peptide analogs to proteolysis can be readily measured. Additionally, the functional activity of the GLP-1 peptide analogs can be demonstrated by examining the insulinotropic properties of the peptide hormone analogs. Insulinotrophic activity may be determined, for example, by providing a given peptide analog to animal cells, or injecting that analog into animals and monitoring the release of immunoreactive insulin (IRI) into the media or circulatory system of the animal, respectively. The presence of IRI can be detected through the use of a radioimmunoassay which can specifically detect insulin.

The db/db mouse is a genetically obese and diabetic strain of mouse. The db/db mouse develops hyperglycemia and hyperinsulinemia concomitant with its development of obesity and thus serves as a model of obese type 2 diabetes (NIDDM). The db/db mice can be purchased from, for example, The Jackson Laboratories (Bar Harbor, Me.). In an exemplary embodiment, for treatment of the mice with a regimen including a peptide hormone analog or control, sub-orbital sinus blood samples are taken before and at some time (e.g., 60 minutes) after dosing of each animal. Blood glucose measurements can be made by any of several conventional techniques, such as using a glucose meter. The blood glucose levels of the control and peptide hormone analog dosed animals are compared The metabolic fate of exogenous GLP-1 analog can also be followed in either nondiabetic and type II diabetic subjects, and the effect of a candidate analog determined. For instance, a combination of high-pressure liquid chromatography (HPLC), specific radioimmunoassays (RLAs), and an enzyme-linked immunosorbent assay (ELISA), can be used, whereby intact biologically active GLP-1 and its metabolites can be detected. See, for example, Deacon et al. (1995) *Diabetes* 44:1126-1131. To illustrate, after GLP-1 analog administration, the intact peptide can be measured using an $NH_2$-terminally directed RIA or ELISA, while the difference in concentration between these assays and a $CO_2H$-terminal-specific RIA allowed determination of $NH_2$-terminally truncated metabolites. Without the analog, subcutaneous GLP-1 is rapidly degraded in a time-dependent manner, forming a metabolite which co-elutes on HPLC with GLP-I(9-36) amide and has the same immunoreactive profile. For instance, thirty minutes after subcutaneous GLP-1 administration to diabetic patients (n is 8), the metabolite accounted for 88.5+1.9% of the increase in plasma immunoreactivity determined by the $CO_2H$-terminal RIA, which was higher than the levels measured in healthy subjects (78.4+3.2%; n=8; P<0.05). See Deacon et al., supra. Intravenously infused GLP-I was also extensively degraded.

Other methods of measuring insulinotropic activities of GLP-1 analogs are disclosed in U.S. Pat. No. 5,545,618.

(d) Pharmaceutical Preparations

For therapeutic use, the chosen $P'_1$ analog is formulated with a carrier that is pharmaceutically acceptable and is appropriate for administering a therapeutically effective amount of the $P'_1$ analog to a subject using a dosage adapted for a chosen route of administration, i.e., oral, intravenous, or parenteral, so as to deliver the peptide to the desired tissue. In certain embodiments, the analogs are non-pyrogenic, i.e., do not trigger elevation of a patient's body temperature by more than a clinically acceptable amount. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion, e.g., when used as liquid nutritional supplements for patients on total parenteral nutrition therapy, or by injection, e.g., sub-cutaneously, intramuscularly or intravenously, and are accordingly utilized as aqueous solutions in sterile and pyrogen-free form and optionally buffered to physiologically tolerable pH, e.g., a slightly acidic or physiological pH. Thus, the compounds may be administered in a vehicle such as distilled water or, more desirably, in saline, phosphate buffered saline or 5% dextrose solution. Water solubility of the $P'_1$ analog may be enhanced, if desired, by incorporating a solubility enhancer, such as acetic acid or sodium hydroxide.

The $P'_1$ analogs of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, or toluenesulfonic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids).

A therapeutically effective amount of a $P'_1$ analog of this invention and a pharmaceutically acceptable carrier substance (e.g., magnesium carbonate, lactose, or a phospholipid with which the therapeutic analog can form a micelle) together form a therapeutic composition (e.g., a pill, tablet, capsule, or liquid) for administration (e.g., orally, intravenously, transdermally, pulmonarily, vaginally, subcutaneously, nasally, iontophoretically, intratracheally, intracranially, intramyocardially, intraperidardially, intramuscularly) to a subject. The pill, tablet, or capsule that is to be administered orally can be coated with a substance for protecting the active composition from the gastric acid or intestinal enzymes in the stomach for a period of time sufficient to allow it to pass undigested into the small intestine. The therapeutic composition can also be in the form of a biodegradable or nonbiodegradable sustained release formulation for subcutaneous or intramuscular administration. See, e.g., U.S. patent Ser. Nos. 3,773,919 and 4,767,628 and PCT Application No. WO 94/15587. Continuous administration can also be achieved using an implantable or external pump (e.g., INFUSAID™ pump). The administration can also be conducted intermittently, e.g., single daily injection, or continuously at a low dose, e.g., sustained release formulation.

Therapeutic or diagnostic compositions of the invention are administered to an individual in amounts sufficient to treat or diagnos disorders. The effective dose of a peptide of the present invention for treating the above-mentioned diseases or disorders varies depending upon the manner of administration, the age and the body weight of the subject, and the condition of the subject to be treated, and ultimately will be decided by the attending physician or veterinarian.

Also contemplated within the scope of this invention is a peptide covered by the above generic formula for use in treating diseases or disorders associated with aberrant glucose metabolism, lipid metabolism or eating disorder.

Other features and advantages of the present invention will be apparent from the detailed description and from the claims.

(v) Methods of Use (1) Diagnostic Uses

The peptide hormone analogs of the invention may be used in radiolabeled or unlabeled form to diagnose or treat a variety of disease states including but not limited to those associated with glucose metabolism, lipid metabolism, food intake, and hypertension.

Preferably, radiolabeled complexes of the compounds of the invention are used for such diagnoses and treatments. Radiolabeled embodiments, of the compounds of the invention may be used in radioisotope guided surgery, as described in WO 93/18797 and in Woltering, et al. (1994) Surgery 116, 1139-1147. In a preferred embodiment, a complex of a .gamma.-emitting radionuclide such as $^{99}$Tc and a compound of the invention is used to diagnose an SSTR-expressing tumor, and subsequently, a complex of β-emitting radionuclide such as $^{188}$Re or $^{186}$Re with the compound is used to treat the tumor.

For diagnostic purposes, an effective diagnostic amount of the diagnostic or radiodiagnostic agent of the invention is administered, preferably intravenously. An effective diagnostic amount is defined as the amount of diagnostic or radiodiagnostic agent necessary to effect localization and detection of the label in vivo using conventional methodologies such as magnetic resonance, computerized tomography, gamma scintigraphy, SPECT, PET, and the like.

For diagnosis using scintigraphic imaging, preferably, $^{99}$Tc-labeled compounds of the invention are administered in a single unit injectable dose. The $^{99}$Tc-labeled compounds provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 50 mCi. The solution to be injected at unit dosage is from about 0.01 mL to about 10 mL. After intravenous administration, imaging in vivo can take place in a matter of a few minutes. However, imaging can take place, if desired, hours or even longer after the radiolabeled compound is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

(2) Methods of Treatment

P'$_1$ analogs provide improved methods of treating any disease or condition that can be treated with a given polypeptide therapeutic composition, wherein the polypeptide is normally cleaved in vivo by a proteinase. Given that proteolysis decreases or eliminates the availability of the therapeutic, and in some instances leads to the production of functionally antagonistic products, the safety and efficacy of many polypeptide therapeutics which can be used to treat particular diseases and conditions is greatly compromised. Accordingly, the methods and compositions of proteinase resistant P'$_1$ analogs provides improved methods of treating any of a number of diverse diseases and conditions.

To more explicitly illustrate the applicability of P'$_1$ analogs in improved methods of treating a variety of diseases and conditions, we provide the following non-limiting examples. In certain embodiments, the P'$_1$ analogs of the present invention are peptide hormone analogs. These peptide hormones possess, in certain embodiments, the ability to lower blood glucose levels, to relieve obesity, to alleviate impaired glucose tolerance, to inhibit hepatic glucose neogenesis, and to lower blood lipid levels and to inhibit aldose reductase. They are thus useful for the prevention and/or therapy of congestive heart failure, hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis. Thus one aspect of the present invention is a method for treating a disease in a patient or subject comprising administering a therapeutically effective amount of one or more peptide hormone analogs, such as the peptide hormone analogs disclosed herein.

In certain embodiments, the proteolysis-resistant analogs for use in a method of treatment comprise P'$_1$ analogs of active GLP-1 peptides. GLP-1 peptides of various lengths are known to be biologically active including: GLP-1(7-34), GLP-1(7-35), GLP-1(7-36), and GLP-1(7-37) the sequences of which are listed below:

```
GLP-1 (7-37):                              (SEQ ID NO: 1)
HAE GTFTSDVSSY LEGQAAKEFI AWLVKGRG;

GLP-1 (7-36):                              (SEQ ID NO: 2)
HAE GTFTSDVSSY LEGQAAKEFI AWLVKGR(-NH₂);

GLP-1 (7-35):                              (SEQ ID NO: 29)
HAE GTFTSDVSSY LEGQAAKEFI AWLVK;
and GLP-1 (7-34):                              (SEQ ID NO: 30)
HAE GTFTSDVSSY LEGQAAKEFI AWLV.
```

In certain embodiments, the present invention relates to a method for modifying glucose metabolism. P'$_1$ analogs of GLP-1 peptides may be administered to patient suffering from diabetes mellitus. Diabetes mellitus is a disease characterized by hyperglycemia occurring from a relative or absolute decrease in insulin secretion, decreased insulin sensitivity, or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum, or whole blood) for several predetermined points in time.

Thus, in one aspect, the present invention relates to therapeutic and related uses of proteolysis-resistant GLP-1 analogs for treating heart-related ailments, hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis.

In certain embodiments, the subject GLP-1 analogs can be used as part of treatment regimens for various heart-related ailments. Exemplary heart related ailments include myocardial infarction, ischemia-reperfusion injury, congestive heart failure, and cardiac arrest. The subject GLP-1 analogs can also be used in the prevention of heart related ailments.

In certain embodiments, the subject analogs can be used to induce arousal for the treatment or amelioration of depression, schizoaffective disorders, sleep apnea, attention deficit syndromes with poor concentration, memory loss, forgetfulness, and narcolepsy.

In certain embodiments, therapeutically effective amounts of proteolysis-resistant GLP-2 analogs may be administered to patients suffering from gastrointestinal diseases. It has been determined that GLP-2 acts as a trophic agent, to promote growth of gastrointestinal tissue. The effect of GLP-2 is marked particularly by increased growth of the small bowel, and is therefore herein referred to as an "intestinotrophic" effect.

Thus, in one aspect, the present invention relates to therapeutic and related uses of GLP-2 analogs for promoting the growth and proliferation of gastrointestinal tissue, most particularly small bowel tissue. For instance, the subject method can be used as part of a regimen for treating injury, inflammation or resection of intestinal tissue, e.g., where enhanced growth and repair of the intestinal mucosal epithelial is desired.

With respect to small bowel tissue, such growth is measured conveniently as an increase in small bowel mass and length, relative to an untreated control. The effect of subject GLP-2 analogs on small bowel also manifests as an increase in the height of the crypt plus villus axis. Such activity is referred to herein as an "intestinotrophic" activity. The efficacy of the subject method may also be detectable as an increase in crypt cell proliferation and/or a decrease in small bowel epithelium apoptosis. These cellular effects may be noted most significantly in relation to the jejunum, including the distal jejunum and particularly the proximal jejunum, and also in the distal ileum. A compound is considered to have "intestinotrophic effect" if a test animal exhibits significantly increased small bowel weight, increased height of the crypt plus villus axis, or increased crypt cell proliferation or decreased small bowel epithelium apoptosis when treated with the compound (or genetically engineered to express it themselves). A model suitable for determining such gastrointestinal growth is described by U.S. Pat. No. 5,834,428.

In general, patients who would benefit from either increased small intestinal mass and consequent increased small bowel mucosal function are candidates for treatment by the subject method. Particular conditions that may be treated include the various forms of sprue including celiac sprue which results from a toxic reaction to α-gliadin from wheat, and is marked by a tremendous loss of village of the bowel; tropical sprue which results from infection and is marked by partial flattening of the village; hypogammaglobulinemic sprue which is observed commonly in patients with common variable immunodeficiency or hypogammaglobulinemia and is marked by significant decrease in villus height. The therapeutic efficacy of the treatment may be monitored by enteric biopsy to examine the villus morphology, by biochemical assessment of nutrient absorption, by patient weight gain, or by amelioration of the symptoms associated with these conditions. Other conditions that may be treated by the subject method, or for which the subject method may be useful prophylactically, include radiation enteritis, infectious or post-infectious enteritis, regional enteritis (Crohn's disease), small intestinal damage due to toxic or other chemotherapeutic agents, and patients with short bowel syndrome.

More generally, the present invention provides a therapeutic method for treating digestive tract diseases. The term "digestive tract" as used herein means a tube through which food passes, including stomach and intestine. The term "digestive tract diseases" as used herein means diseases accompanied by a qualitative or quantitative abnormality in the digestive tract mucosa, which include, e.g., ulceric or inflammatory bowel disease; congenital or acquired digestion and absorption disorder including malabsorption syndrome; disease caused by loss of a mucosal barrier function of the gut; and protein-losing gastroenteropathy. The ulceric disease includes, e.g., gastric ulcer, duodenal ulcer, small intestinal ulcer, colonic ulcer and rectal ulcer. The inflammatory bowel disease includes, e.g., esophagitis, gastritis, duodenitis, enteritis, colitis, Crohn's disease, proctitis, gastrointestinal Behcet, radiation enteritis, radiation colitis, radiation proctitis, enteritis and medicamentosa. The malabsorption syndromes includes the essential malabsorption syndrome such as disaccharide-decomposing enzyme deficiency, glucose-galactose malabsorption, fructose malabsorption; secondary malabsorption syndromes, e.g., the disorder caused by a mucosal atrophy in the digestive tract through the intravenous or parenteral nutrition or elemental diet, the disease caused by the resection and shunt of the small intestine such as short gut syndrome, cul-de-sac syndrome; and indigestible malabsorption syndrome such as the disease caused by resection of the stomach, e.g., dumping syndrome.

The term "therapeutic agent for digestive tract diseases" as used herein means the agents for the prevention and treatment of the digestive tract diseases, which include, e.g., the therapeutic agent for digestive tract ulcer, the therapeutic agent for inflammatory digestive tract disease, the therapeutic agent for mucosal atrophy in the digestive tract and the therapeutic agent for digestive tract wound, the amelioration agent for the function of the digestive tract including the agent for recovery of the mucosal barrier function and the amelioration agent for digestive and absorptive function. The ulcers include digestive ulcers and erosions, acute ulcers, namely, acute mucosal lesions.

The subject method, because of promoting proliferation of intestinal mucosa, can be used in the treatment and prevention of pathologic conditions of insufficiency in digestion and absorption, that is, treatment and prevention of mucosal atrophy or treatment of hypoplasia of the digestive tract tissues and decrease in these tissues by surgical removal as well as improvement of digestion and absorption. Further, the subject method can be used in the treatment of pathologic mucosal conditions due to inflammatory diseases such as enteritis, Crohn's disease and ulceric colitis and also in the treatment of reduction in function of the digestive tract after operation, for example, in dumping syndrome as well as in the treatment of duodenal ulcer in conjunction with the inhibition of peristalsis of the stomach and rapid migration of food from the stomach to the jejunum. Furthermore, glicentin can effectively be used in promoting cure of surgical invasion as well as in improving functions of the digestive tract. Thus, the present invention also provides a therapeutic agent for atrophy of the digestive tract mucosa, a therapeutic agent for wounds in the digestive tract and a drug for improving functions of the digestive tract which comprise glicentin as active ingredients.

Additionally, the subject method can be used to alter the pharmacokinetics of pancreatic peptide, Peptide YY and neuropeptide Y, all of which are members of the pancreatic polypeptide family. Specifically, DPP IV has been implicated in the processing of those peptides in a manner which alters receptor selectivity, and thus DPP IV resistant analogs of each of these peptides can be readily designed.

Neuropeptide Y (NPY) is believed to act in the regulation of vascular smooth muscle tone, as well as regulation of blood pressure. NPY also decreases cardiac contractility. NPY is also the most powerful appetite stimulant known (Wilding et al., (1992) J Endocrinology 132:299-302). The centrally evoked food intake (appetite stimulation) effect is predominantly mediated by NPY Y1 receptors and causes increase in body fat stores (Stanley et al., (1989) Physiology and Behavior 46:173-177). By way of example, one possible use of NPY analogs is in the manufacture of therapeutics that increase appetite. Although much of the world strives to lose weight, in a number of contexts, the goal is to gain weight. The incidence of eating disorders is on the rise around the world. Over time, individuals with eating disorders suffer from a pathological lose of appetite, and this lose of appetite makes re-feeding extremely difficult. Such difficulty often persists even when the individual's weight has reached a life-threateningly low level. Accordingly, the use of agents which stimulate the appetite would greatly enhance the ability of health care providers to encourage and support re-feeding of severely malnourished eating disorder patients.

The difficulty encountered by individuals attempting to re-feed following prolonged periods of malnutrition is not limited to individuals with eating disorders. Malnutrition due to any cause can result in a serious suppression of appetite and this can be a barrier to quickly and easily facilitating proper nutrition in these individuals. Therapeutics that stimulate appetite would have great utility in the treatment of malnourished individuals.

Loss of appetite and wasting syndromes are often associated with other diseases and conditions. For example, patients with various forms of cancer and AIDS often experience wasting. This significant weight loss, as well as loss of muscle mass, can lead to a variety of other complications including loss of energy and further suppression of the immune system. Accordingly, therapeutics which help to counter the loss of appetite and wasting associated with other diseases and treatments would greatly improve the quality of life of patients battling any of a number of diseases.

A final example pertains to the administration of therapeutics that stimulate appetite and stimulate weight gain in the agricultural arena. Such agents could be used to help raise animals, such as commercial livestock, with a higher average weight and/or a higher average fat content. By way of example, such therapeutics could be administered, for example in animal feed or water, to cows, pigs, chickens, sheep, turkeys, goat, buffalo, ostrich, and the like to poduce larger animals for sale in the food industry.

Peptide YY (PYY) and pancreatic polypeptide (PP) are involved in eating disorders, gastrointestinal disorders, and pancreatic tumors. (See U.S. Pat. No. 5,574,010)

DPP IV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin (Kubiak et al. (1994) *Peptide Res* 7:153). GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

The invention contemplates the use of $P'_1$ analogs in methods of treatment wherein the $P'_1$ analog alone constitutes the therapeutic regimen, as well as methods of treatment that utilize administration of one or more $P'_1$ analogs as part of a more complex multi-factorial therapeutic regimen. For example, in the case of methods of treating diabetes and/or complications of diabetes, the present invention contemplates methods of treating diabetes by administering a $P'_1$ analog such as a GLP-1 analog. The present invention further contemplates that, in some circumstances, it may be preferably to administer more than one $P'_1$ analog. For example, the method of treatment may comprise administration of two or more $P'_1$ analogs. Such $P'_1$ analogs may be analogs of the same polypeptide (e.g., two different GLP-1 analogs), or may be analogs of distinct polypeptides. Furthermore the invention contemplates that administratin of one or more $P'_1$ analogs may be used as part of a complex therapeutic regimen. In the case of a method of treating diabetes or complications of diabetes, an exemplary therapeutic regimen may include administration of one or more $P'_1$ analog, administration of insulin, modulation of diet, and modulation of exercise.

In still a further example of a multi-faceted therapeutic regimen, the invention contemplates the administration of one or more $P'_1$ analogs and one or more agents that inhibit the enzymatic activity of the particular enzyme that endogenouely cleaves the native protein. In the case of GLP-1, an exemplary method would comprise administration of one or more peptide analogs with one or more inhibitors of DPP IV. Inhibitors of a particular enzyme may be specific (e.g., an inhibitor that modulates only the activity of DPP IV) or the inhibitor may be more promiscuous (e.g., an inhibitor that modulates the activity of multiple serine proteases). Additionally, the invention contemplates the administration of one or more $P'_1$ analogs and one or more enzymes that degrade the particular enzyme that endogenouely cleaves the native protein. In the case of GLP-1, an exemplary method would comprise administration of one or more peptide analogs with one or more enzymes that degrade DPP IV. Such enzymes may be specific (e.g., an enzyme that only degrades DPP IV) or the enzyme may degrade multiple other protein (e.g., an enzyme that degrades several serine proteases).

(f) Business Methods

Other aspects of the invention provide for certain methods of doing business. In particular, practicing the methods of the invention may identify certain peptidase resistant $P'_1$ analogs, such as peptide hormone analogs. This technical step, when combined with one of more additional steps, provides for novel approaches to conduct a pharmaceutical, agrochemical, biotechnological, or preferably a life-science business. For example, $P'_1$ analogs according to the present invention can be tested for efficacy as therapeutics in a variety of disease models, and the potential therapeutic compositions can then be tested for toxicity and other safety-profiling before formulating, packaging and subsequently marketing the resulting formulation for the treatment of disease. Alternatively, the rights to develop and market such formulations or to conduct such steps may be licensed to a third party for consideration. In certain other aspects of the invention, the $P'_1$ analogs thus identified may have utility in the form of information that can be provided to a third party for consideration such that an improved understanding of the function or side effects of said $P'_1$ analogs in a biological or therapeutic context is obtained.

In certain embodiments, the initially identified $P'_1$ analog can be subjected to further optimization, e.g., to further refine the structure of a lead analog. Such optimization may lead to the development of analogs that combine maximal resistance to proteolysis with other diserable pharmacological characteristics including: solubility, permeability, bioavailability, toxicity, mutagenicity, and pharmacokinetics.

Structural modifications are made to a lead analog to address issues with the parameters listed above. These modifications however, must take into account possible effects on the analog's potency and activity. For example, if the toxicity of a lead analog is high when tested in an animal model, modifications can be made to the analog in an effort to decrease toxicity while maintaining the desired characteristic of proteinase resistance.

Candidate analogs (whether or not said analogs are modified to alter to improve in vivo characteristics) or combinations thereof, must be tested for efficacy and toxicity in animal models. Such therapeutic profiling is commonly employed in the pharmaceutical arts. Before testing an experimental therapeutic in humans, extensive therapeutic profiling (preclinical testing) must be completed to establish initial parameters for safety and efficacy. Preclinical testing establishes a mechanism of action for the therapeutic, its bioavailability, absorption, distribution, metabolism, and elimination through studies performed in vitro (that is, in test tubes, beakers, petri dishes, etc.) and in animals. Animal studies are used to assess whether the therapeutic will provide the desired results. Varying doses of the experimental therapeutic are administered to test the therapeutic's efficacy, identify harmful side-effects that may occur, and evaluate toxicity.

Briefly, one of skill in the art will recognize that the identification of a candidate, proteinase resistant analog is a first step in developing a pharmaceutical preparation useful for administration. Administration of an amount of a pharmaceutical preparation comprising said $P'_1$ analog effective to treat a condition or disease must be both safe and effective. Early stage drug trials, routinely used in the art, help to address concerns of the safety and efficacy of a potential pharmaceutical. In the specific case of a $P'_1$ analog, efficacy of the pharmaceutical preparation could be readily evaluated first in cell culture, and then in a mouse or rat model. Cell culture systems and animal models appropriate for the particular disease indication for which a given $P'_1$ analog will be used can be readily selected by one of skill in the art. Briefly, mice or rats could be administered varying doses of said pharmaceutical preparations over various time schedules. The route of administration would be appropriately selected based on the particular characteristics of the agent and on the cell type to which delivery of the $P'_1$ analog is desired. Control mice can be administered a placebo (e.g., carrier or excipient alone).

In one embodiment, the step of therapeutic profiling includes toxicity testing of analogs in cell cultures and in animals; analysis of pharmacokinetics and metabolism of the candidate analog; and determination of efficacy in animal models of diseases. In certain instances, the method can include analyzing structure-activity relationship and optimizing lead analogs based on efficacy, safety and pharmacokinetic profiles. The goal of such steps is the selection of analog candidates for pre-clinical studies to lead to filing of Investigational New Drug applications ("IND") with the FDA prior to human clinical trials.

Between lead optimization and therapeutic profiling, one goal is to develop a $P'_1$ analog that is resistant to a particular protease and can be administered with minimal side-effects. In the case of analogs for in vitro use, exemplary analogs should not be exceptionally toxic to cells in culture, should not be mutagenic to cells in culture, and should not be carcinogenic to cells in culture. In the case of analogs for in vivo use, exemplary analogs should not be exceptionally toxic (e.g., should have only tolerable side-effects when administered to patients), should not be mutagenic, and should not be carcinogenic.

By toxicity profiling is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made by the Food and Drug Administration during the regulatory approval process. This determination does not follow hard and fast rules, and that which is considered an acceptable side effect varies due to factors including: (a) the severity of the condition being treated, and (b) the availability of other treatments and the side-effects currently associated with these available treatments. For example, the term cancer encompasses a complex family of disease states related to mis-regulated cell growth, proliferation, and differentiation. Many forms of cancer are particularly devastating diseases which cause severe pain, loss of function of the effected tissue, and death. Chemotheraputic drugs are an important part of the standard therapy for many forms of cancer. Although chemotherapeutics themselves can have serious side-effects including hair-loss, severe nausea, weight-loss, and sterility, such side-effects are considered acceptable given the severity of the disease they aim to treat. In the context of the present invention, whether a side-effect is considered significant will depend on the condition to be treated and the availability of other methods to treat that condition.

Toxicity tests can be conducted in tandem with efficacy tests, and mice administered effective doses of the pharmaceutical preparation can be monitored for adverse reactions to the preparation.

One or more proteinase resistant $P'_1$ analogs, which are proven safe and effective in animal studies, can be formulated into a pharmaceutical preparation. Such pharmaceutical preparations can then be marketed, distributed, and sold. Exemplary $P'_1$ analogs and pharmaceutical preparation of such analogs may be marketed and sold alone, or may be sold as a pharmaceutical package and/or kit. Furthermore, in any of the foregoing aspects, a method of conducting a business based on the design of one or more $P'_1$ analogs may optionally include a system for billing a patient and/or the patient's insurance provider, as well as a system for collecting appropriate reimbursement from the patient and/or the patient's insurance provider.

EXAMPLES

The following examples are shown by way of illustration and not by way of limitation.

Example 1

Proteinase Resistant GLP-1 Analogs

Administration of GLP-1 is a candidate therapeutic for diabetes. However, one of the barriers to the efficacy of a treatment based on GLP-1 adminstration is the rapid in vivo degradation of GLP-1 by DPP IV. DPP IV cleaves GLP-1 near the N-terminus between alanine and glutamic acid, and previous studies have indicated that this cleaveage occurs extremely rapidly following administration of exogenous GLP-1 (FIG. 1).

To generate peptide analogs resistant to proteolysis, we constructed analogs containing tetra-substitutions at the P'1 position of GLP-1. In the following examples, GLP1(7-37) was used. Briefly, we made substitutions at the P'1 glutamic acid of GLP-1. Two specific substitutions that were made and tested were 3-dimethyl-aspartate and 3-butyl-methyl-glycine. The resulting GLP-1 analogs were referred to as GLP-1 (3DMA) (wherein the P'1 substitution was 3-dimethyl-aspartate) and GLP-1 (BM) (wherein the P'1 substitution was 3-butyl-methyl-glycine.

Figure 2:
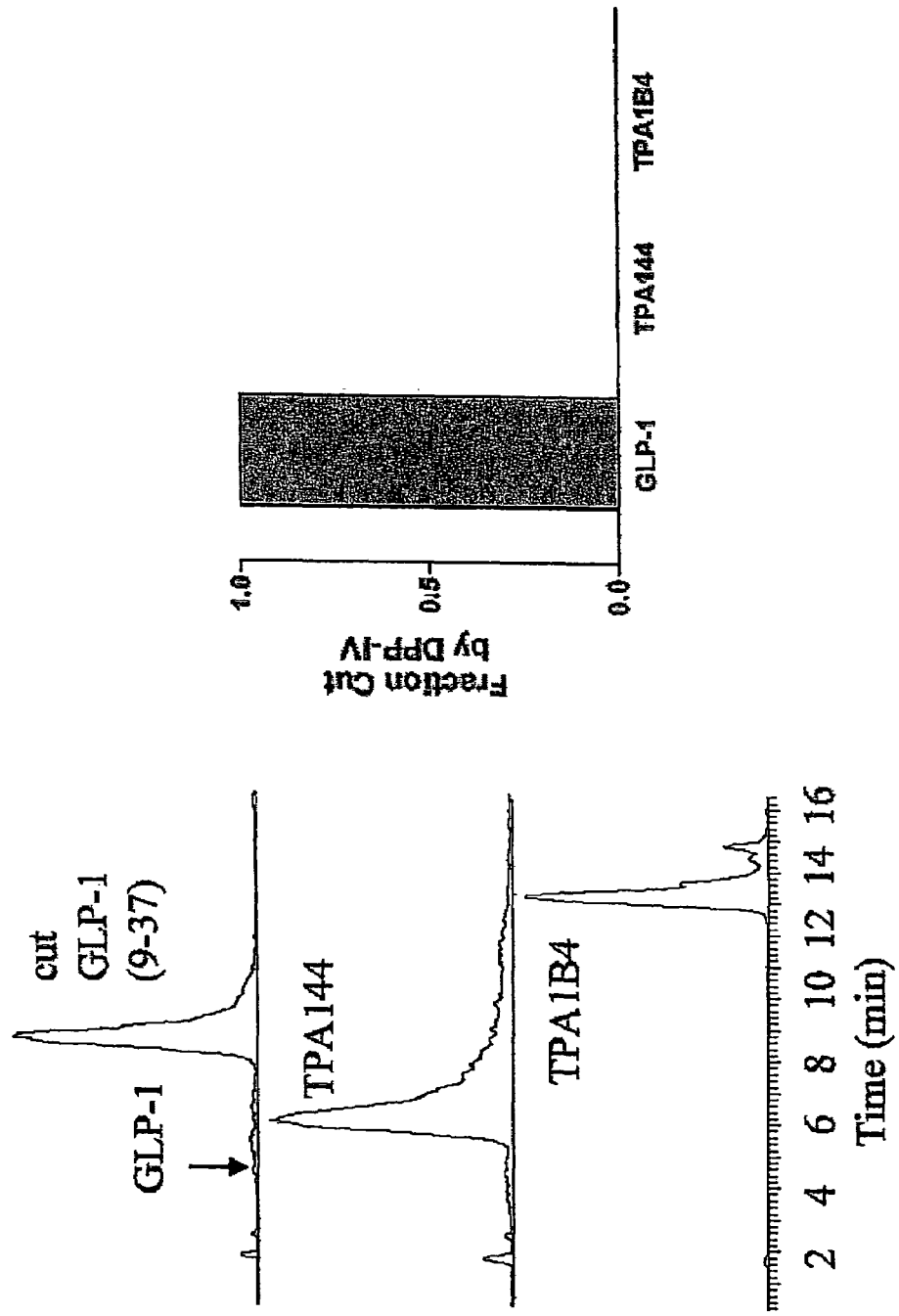
FIG. 2 summarizes HPLC/MS results demonstrating that two different peptide analogs of GLP-1 (7-37) are resistant to cleavage by DPP IV.

FIG. 2 summarizes experiments which demonstrated that both GLP-1 (3DMA) and GLP-1 (BM) were resistant to cleavage by DPP IV in comparison to native GLP-1. However, it is most desirable to produce peptide analogs that are not only resistant to proteolysis, but also retain all or much of the biological activity of the native peptide. Accordingly, we conducted a series of experiments to ascertain whether these GLP-1 analogs which display robust resistance to degradation by DPP IV also retain biological activities of native GLP-1

Example 2

Proteinase Resistant GLP-1 Analogs Retain Functional Activity of Native GLP-1

Figure 3:
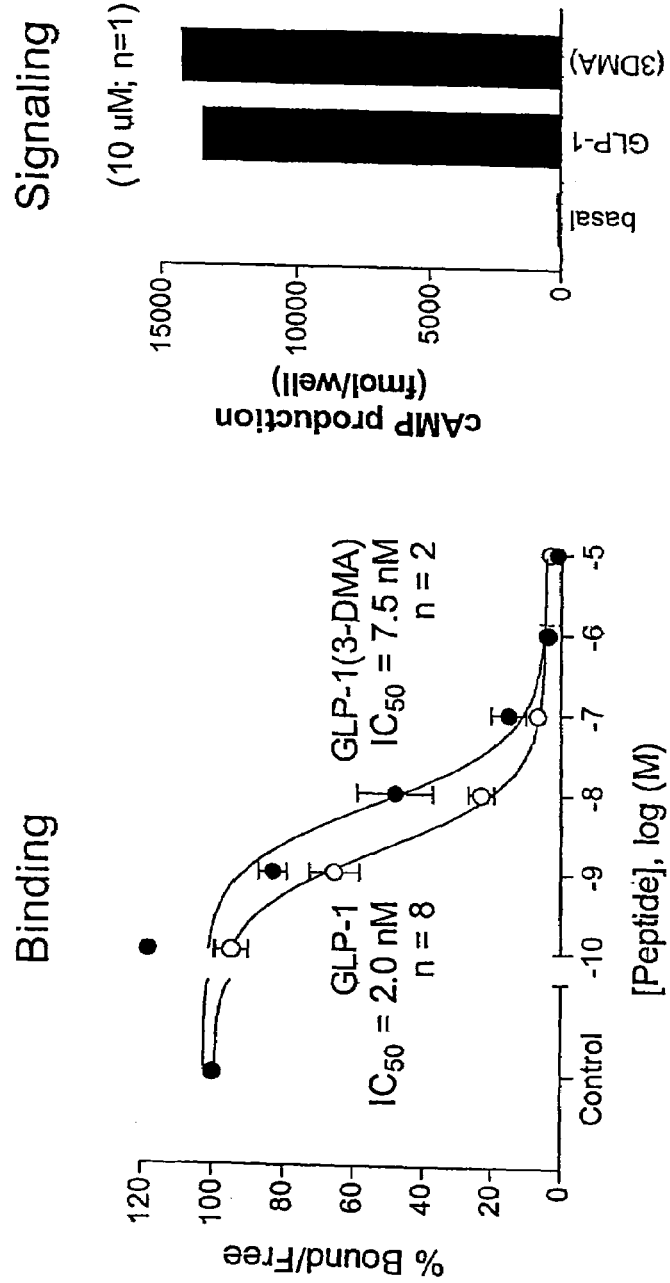
FIG. 3 shows that the 3-dimethyl-aspartate substituted GLP-1 analog maintains functional activities of native GLP-1. The graph at the left shows that GLP-1 and GLP-1 (3-DMA) bind receptor with similar, although not identical, affinities. The graph at the right shows that GLP-1 and GLP-1 (3-DMA) have substantially identical signaling potential as measured by cAMP production following exposure to GLP-1 or GLP-1 analog.
Figure 4:
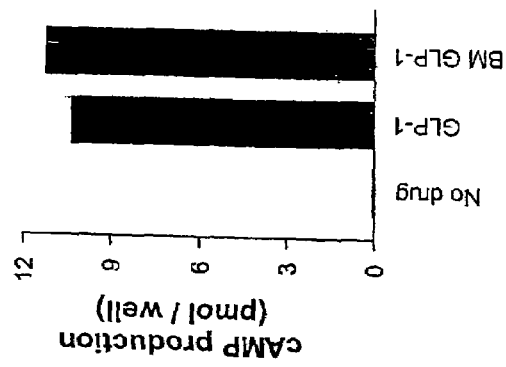
FIG. 4 shows that the 3-butyl-methyl-glycine substituted GLP-1 (GLP-1 (BM)) analog maintains functional activity of native GLP-1. The graph shows that GLP-1 and GLP-1 (BM) have substantially identical signaling potential as measured by cAMP production following exposure to GLP-1 or GLP-1 analog.

We conducted a series of experiments to assess the functional activity of both GLP-1 (3DMA) and GLP-1 (BM) in comparison to native GLP-1 peptide. FIGS. 3-4 summarize the results of these experiements. Briefly, we examined two functional properties of GLP-1: binding of GLP-1 to its receptor and signal transduction as assayed by production of cAMP. FIG. 3 summarizes experiments which examined the activity of GLP-1 (3DMA). The left panel compares the kinetics of receptor binding. We note that GLP-1 (3-DMA) retained the ability to bind the GLP-1 receptor. Additionally, we note that the binding were similar, although not identical, to that of the native peptide.

Further analysis is provided in the right hand panel which summarizes an assay to ascertain whether GLP-1 (3DMA) potentiates GLP-1 signaling in a manner similar to the native peptide. COS-7 cells (approx $10^6$/10 cm plate) were transiently transfected with cDNA encoding the human GLP-1 receptor. One day after transfection, the cells were trypsinized and seeded in 24-well plates (density of approx $10^5$/well). Two days following transfection, the cells were incubated for one hour at room temperature either with native GLP-1 (0.3 µM), GLP-1 (3DMA) (10 µM), or in the absence of either peptide. cAMP content, which correlates with receptor-mediated signaling, was measured in the cell lysate by proximity scintillation radioimmunoassay. As shown in FIG. 3, GLP-1 (3DMA) potentiated signaling via the GLP-1 receptor to an extent indistinguishable from native GLP-1.

FIG. 4 summarizes similar experiments in which the activity of GLP-1 (BM) was measured. Briefly, COS-7 cells (approx $10^{10}$/6 cm plate) were transiently transfected with cDNA encoding the human GLP-1 receptor. One day after transfection, the cells were trypsinized and seeded in 24-well plates (density of approx $10^5$/well). Two days following transfection, the cells were incubated for one hour at room temperature either with native GLP-1 (0.3 µM), GLP-1 (BM) (10 µM), or in the absence of either peptide. cAMP content, which correlates with receptor-mediated signaling, was measured in the cell lysate by proximity scintillation radioimmunoassay. As shown in FIG. 4, GLP-1 (BM) potentiated signaling via the GLP-1 receptor to an extent indistinguishable from native GLP-1.

Example 3

Tert-leucine Substituted GLP-1 Analogs are Resistant to DPP IV Degradation

The data provided in examples 1 and 2 demonstrated that two distinct substitutions at the P'1 position of GLP-1 yielded proteinase resisitant peptide analogs. We have additionally demonstrated that a third substitution at the P'1 positions also yields a proteinase resistant peptide analog. Briefly, the P'1 glutamic acid of GLP-1 (7-37) was substituted with tertiary leucine (TLE), and the ability of DPP IV to cleave this peptide analog was assessed.

Figure 5:
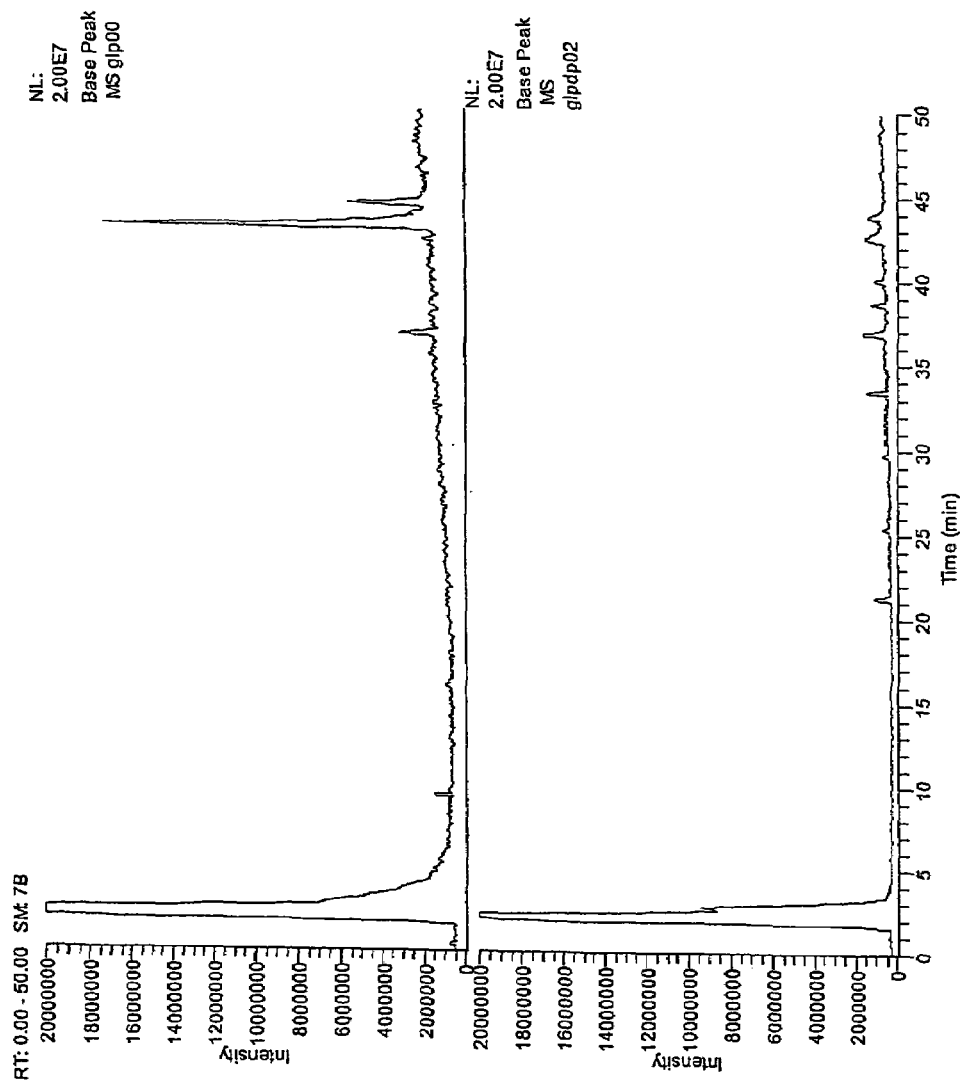
FIG. 5 shows GLP-1 (7-37) amide treated with human DPP-IV for two hours (bottom) compared to untreated peptide (top) by HPLC/MS. Note that treatment of GLP-1 (7-37) with DPP IV resulted in a time dependent loss of peptide

FIG. 5 shows HPLC/MS analysis of GLP-1 (7-37) following two hours of treatment with human DPP IV (bottom chromatogram) in comparison to GLP-1 (7-37) in the absence of proteinase (top chromatogram). As expected, treatment with DPP IV resulted in a time dependent degradation of GLP-1 .

Figure 6:
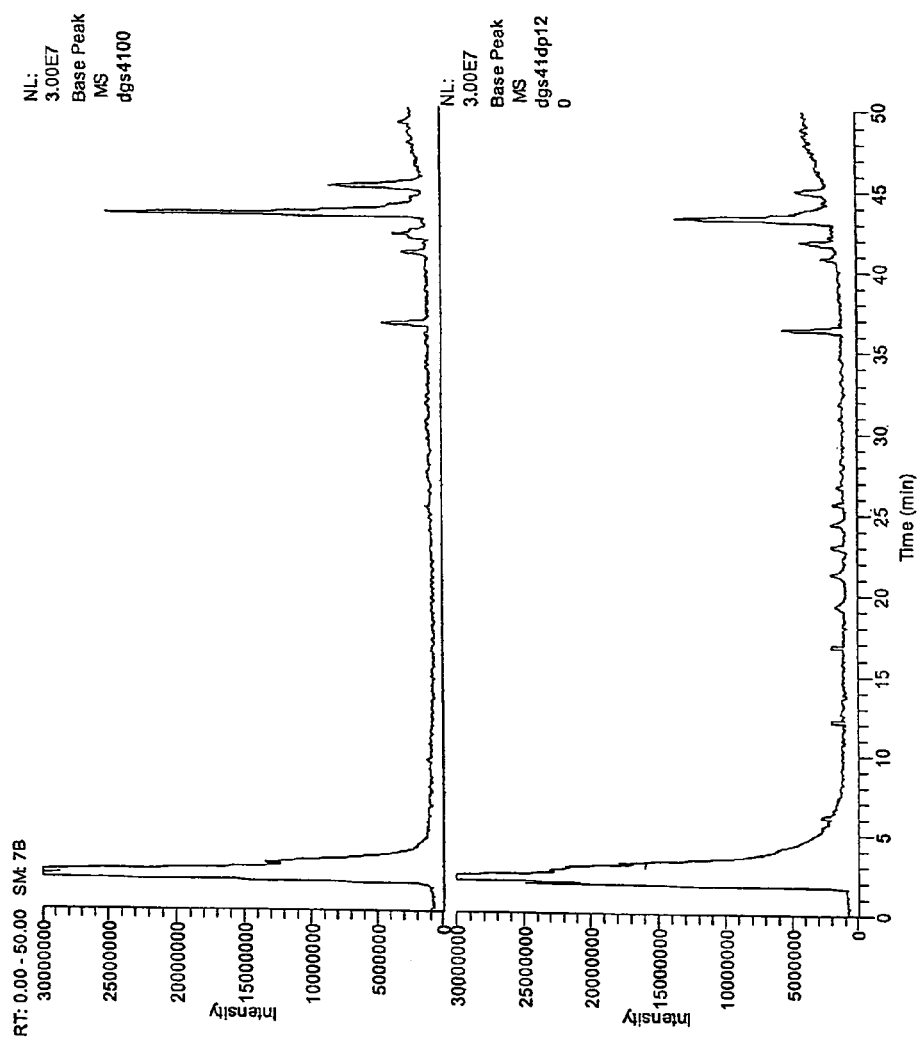
FIG. 6 shows the results of treating a GLP-1 analog containing a tertiary-leucine (TLE) residue in place of the P'1 glutamic acid with human DPP-IV for two hours (bottom) compared to untreated peptide (top) by HPLC/MS. Note that the TLE-GLP1 analog was resistant to degradation by DPP IV.

FIG. 6 shows HPLC/MS analysis of a TLE-modified GLP-1 (7-37) analog. TLE-modified GLP-1 analog was treated with human DPP IV for two hours, and degradation of the analog over time was compared to that of analog in the absence of DPP IV. Comparison of the chromatograms (note: the top panel corresponds to the untreated peptide analog and the bottom panel corresponds to the treated peptide analog) demonstrated that TLE-modified GLP-1 is resistant to degradation by DPP IV.

Example 4

Substitution at the P'1 Position Confers Resistance to Other Proteinases

The foregoing examples provide extensive evidence demonstrating that a variety of substitutions at the P'1 position confer resistance to degradation by the serine protease DPP IV. However, this method of tetra-substitution at the P'1 position to confer proteinase resistance is not specific to substrates cleaved by DPP IV. We have also demonstrated that tetra-substitution at the P'1 position of a model substrate confers resistance to cleavage by thrombin. Although thrombin is a serine proteinase, it recognizes a cleavage site distinct from that of DPP IV, and the results summarized herein indicate the broad applicability of the methods of the present invention for constructing P′$_1$ analogs resistant to degradation by any of a number of proteinases.

FIG. 7 summarizes experiments which demonstrated that substitution of a tertiary leucine (TLE) at the P′$_1$ position of a model thrombin substrate conferred resistance to proteolysis. Briefly, the peptide WALAPRSFA (SEQ ID NO:31) is a model substrate for thrombin. Thrombin cleaves after the arginine residue. Accordingly, the serine residue of this model peptide is the P′1 positions.

WALAPR↓SFA

In the above schematic, the P′1 position serine residue is indicated in bold type and an arrow denotes the site of cleavage by thrombin after the arginine residue.

To test the ability of tetra-substitution at the P′1 position to confer resistance to thrombin proteolysis, we prepared model peptide in which the P′1 position contained a tertiary leucine (TLE). The model peptide analog is represented below, wherein X is used to indicate the TLE substitution.

WALAPRXFA    (SEQ ID NO: 32)

To compare digestion of the model peptide analog by thrombin with that of the native model peptide, peptides were digested for 4 hours at 23° C. with 10 nM thrombin in 0.1 M HEPES pH 8, 0.14 M NaCl, 5 mM CaCl$_2$, 0.5% PEG6000. Following digestion, C18 reverse phase HPLC of the digests was compared to the undigested peptides, and the mass spectra of the major peaks are shown for each cliromatogram in FIG. 7. As shown in FIG. 7, unmodified peptide was efficiently cleaved by thrombin to yield the cleavage product WALAPR (SEQ ID NO: 33). In contrast, the TLE substituted peptide analog was not cleaved by thrombin under these conditions.

Example 5

In-vivo Results for Stable Dimethylaspartate GLP-1 Analogs

Figure 8:
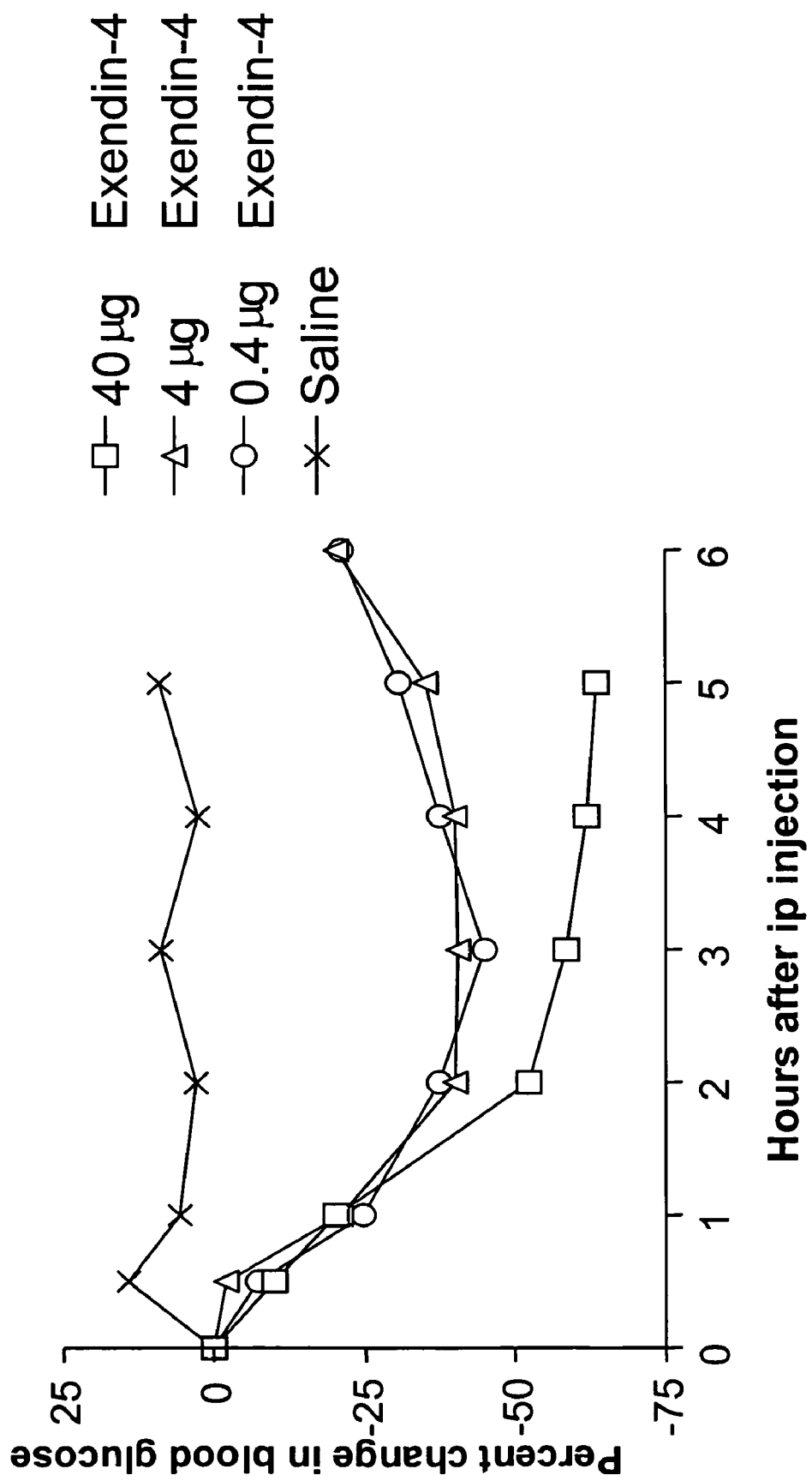
FIG. 8 shows the percent change in blood glucose in diabetic mice for Exendin-4 over time for three different doses (40 μg, 4 μg, and 0.4 μg) as compared to a saline control solution.

FIG. 8 shows the percent change in blood glucose in diabetic mice for Exendin-4 over time for three different doses (40 μg, 4 μg, and 0.4 μg) as compared to a saline control solution.

Figure 9:
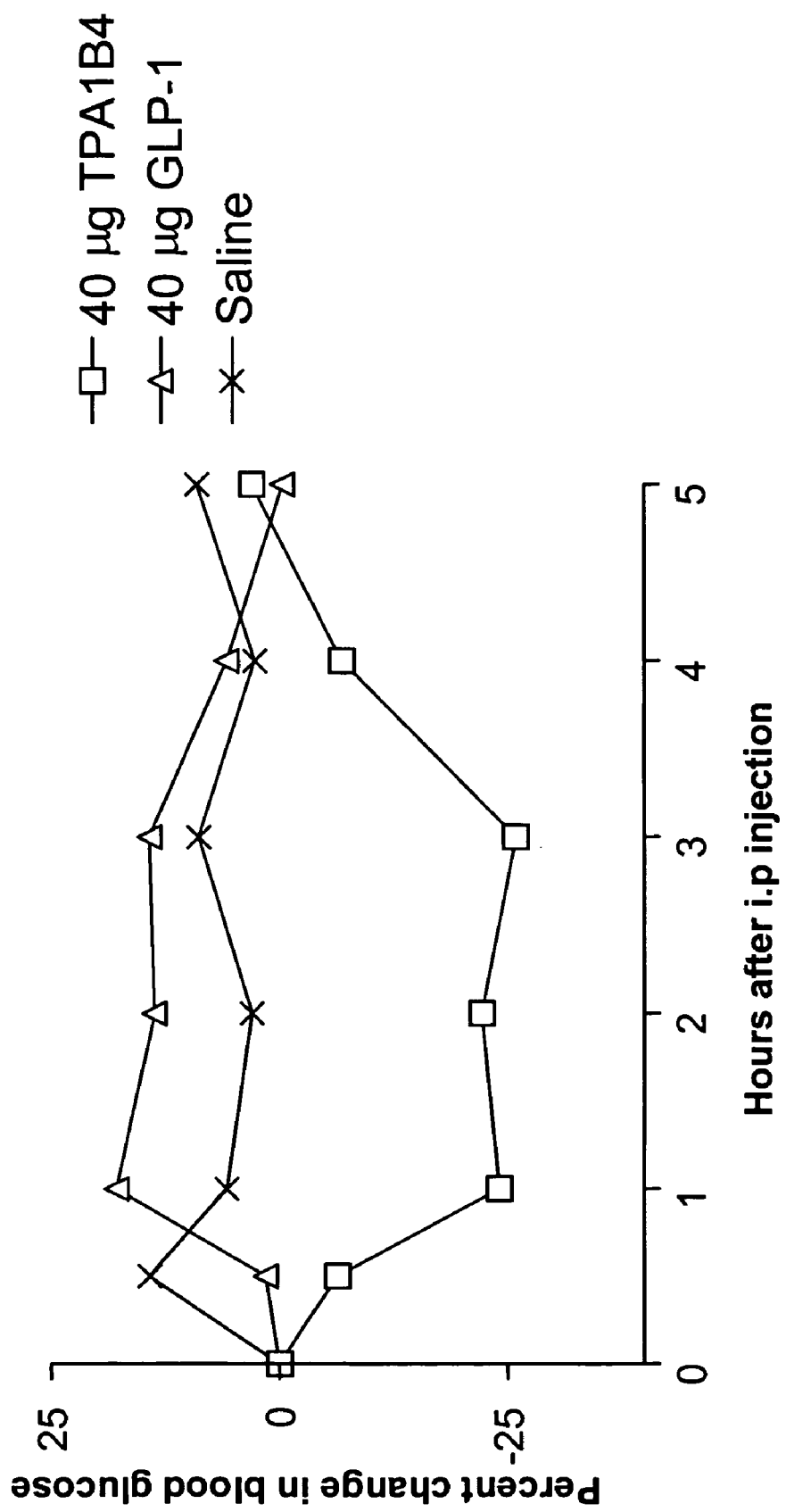
FIG. 9 shows the percent change in blood glucose in diabetic mice for a GLP-1(TPA1B4) analog at a dose of 40 μg over time compared to the percent change in blood glucose for a saline or GLP-1 control.

FIG. 9 shows the percent change in blood glucose in diabetic mice for a GLP-1(TPA1B4) analog at a dose of 40 μg over time compared to the percent change in blood glucose for a saline or GLP-1 control.

Figure 10:
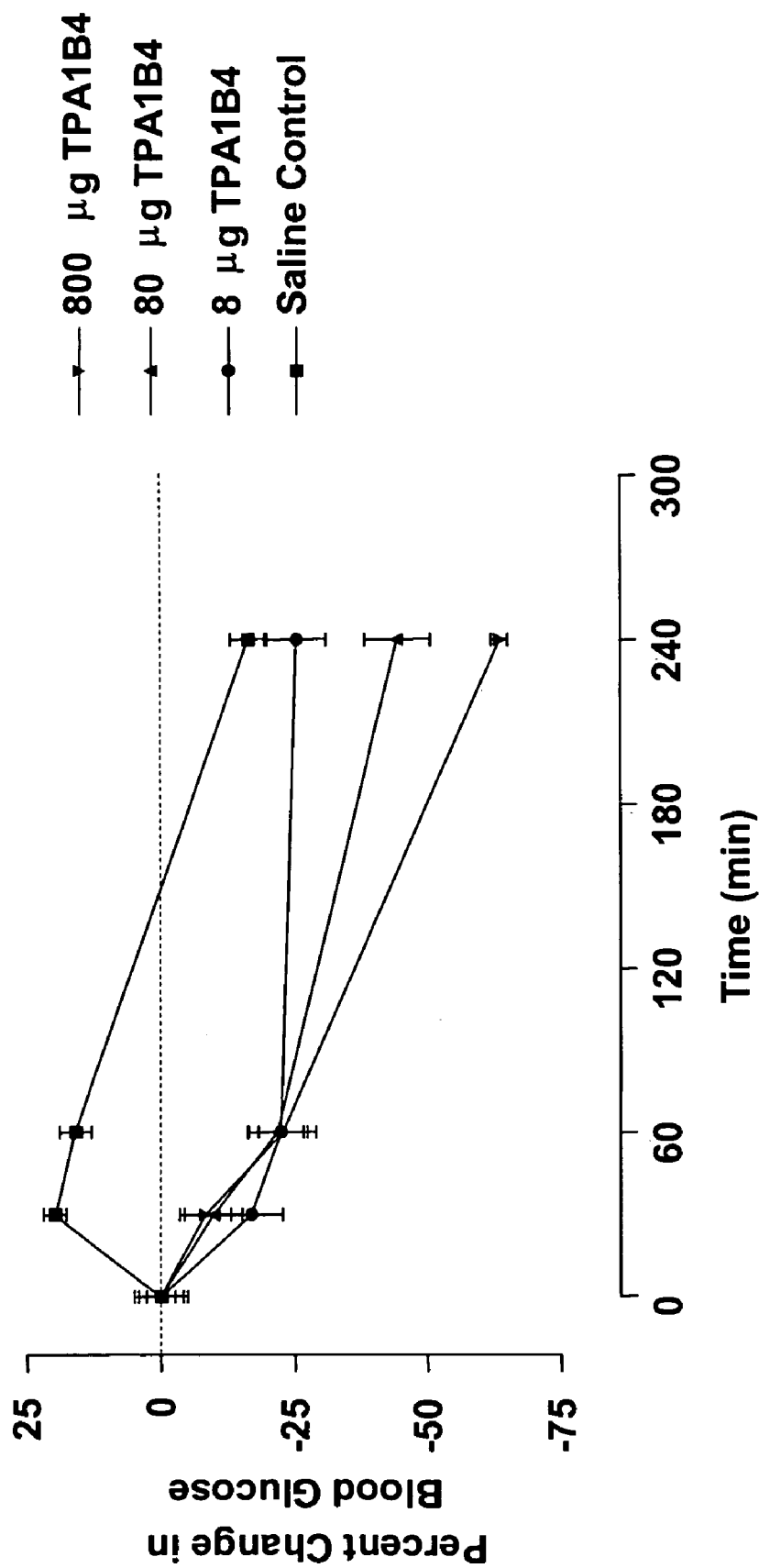
FIG. 10 shows the percent change in blood glucose in diabetic mice for a GLP-1(TPA1B4) analog for three different doses (800 μg, 80 μg, and 8 μg) over time compared to a saline control.

FIG. 10 shows the percent change in blood glucose in diabetic mice for a GLP-1(TPA1B4) analog for three different doses (800 μg, 80 μg, and 8 μg) over time compared to a saline control.

The GLP-1 analog TPA1B4 is an analog of GLP-1 residues 7-36 with a C-terminal amide and a β-dimethyl aspartate residue at position 9. The sequence for TPA1B4 is:

HAXGTFTSDVSSYLEGQAAKEFIAWLVKGR-NH$_2$    (SEQ ID NO: 34)

In-vivo experiments were performed using female BKS.Cg-m+/–LePr(db)/J mice that were purchased at 5-7 weeks of age and allowed to adjust to vivarium conditions for two weeks prior to the start of the experiments. The mice were housed in pressurized, individually ventilated cages. A standard rodent diet was used with food and water provided ad libitum. Blood glucose was measured with a ThereaSense Freestyle blood glucose monitor. The tail vein was nicked with a needle to obtain a small drop of blood (about 10 μL) for each measurement. The GLP-1 analog (TPA1B4) and exendin-4 were dissolved in phosphate buffered saline (PBS) administered by intraperitoneal injection of the indicated dose in 0.2 mL. The saline control for this experiment was a 0.2 mL injection of PBS. Blood glucose measurements were taken at t=0, 30 min, 1 h, 2 h, 3 h, 4 h, 5 h (and 6 h). The values in FIGS. 8 and 9 are the average of five mice.

Figure 11:
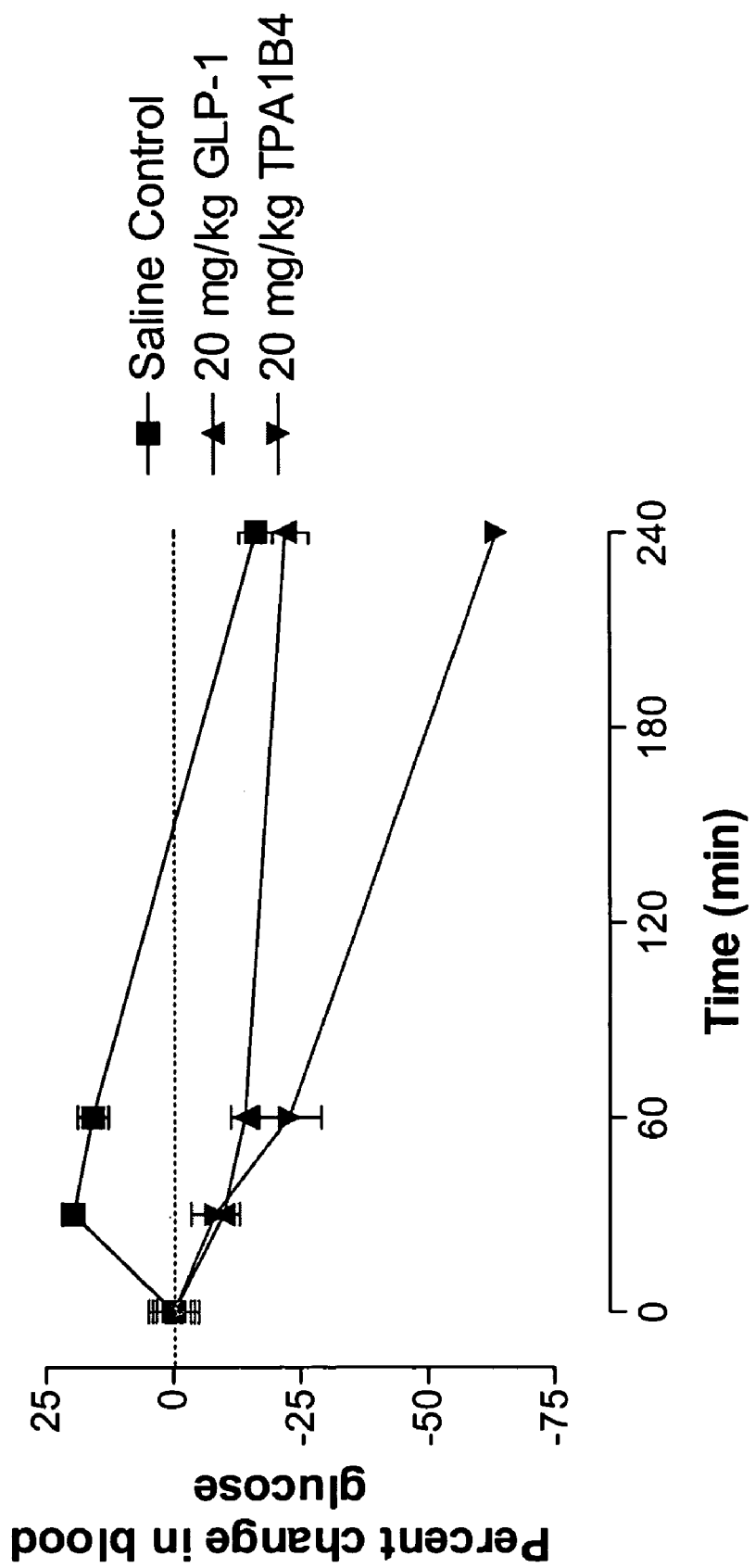
FIG. 11 shows the percent change in blood glucose in diabetic mice for a GLP-1 analog (TPA1B4) at a dose of 20 mg/kg over time compared to the percent change in blood glucose for a saline or GLP-1 control.

FIG. 11 shows the percent change in blood glucose in diabetic mice for a GLP-1 analog (TPA1B4) at a dose of 20 mg/kg over time compared to the percent change in blood glucose for a saline or GLP-1 control.

Figure 12:
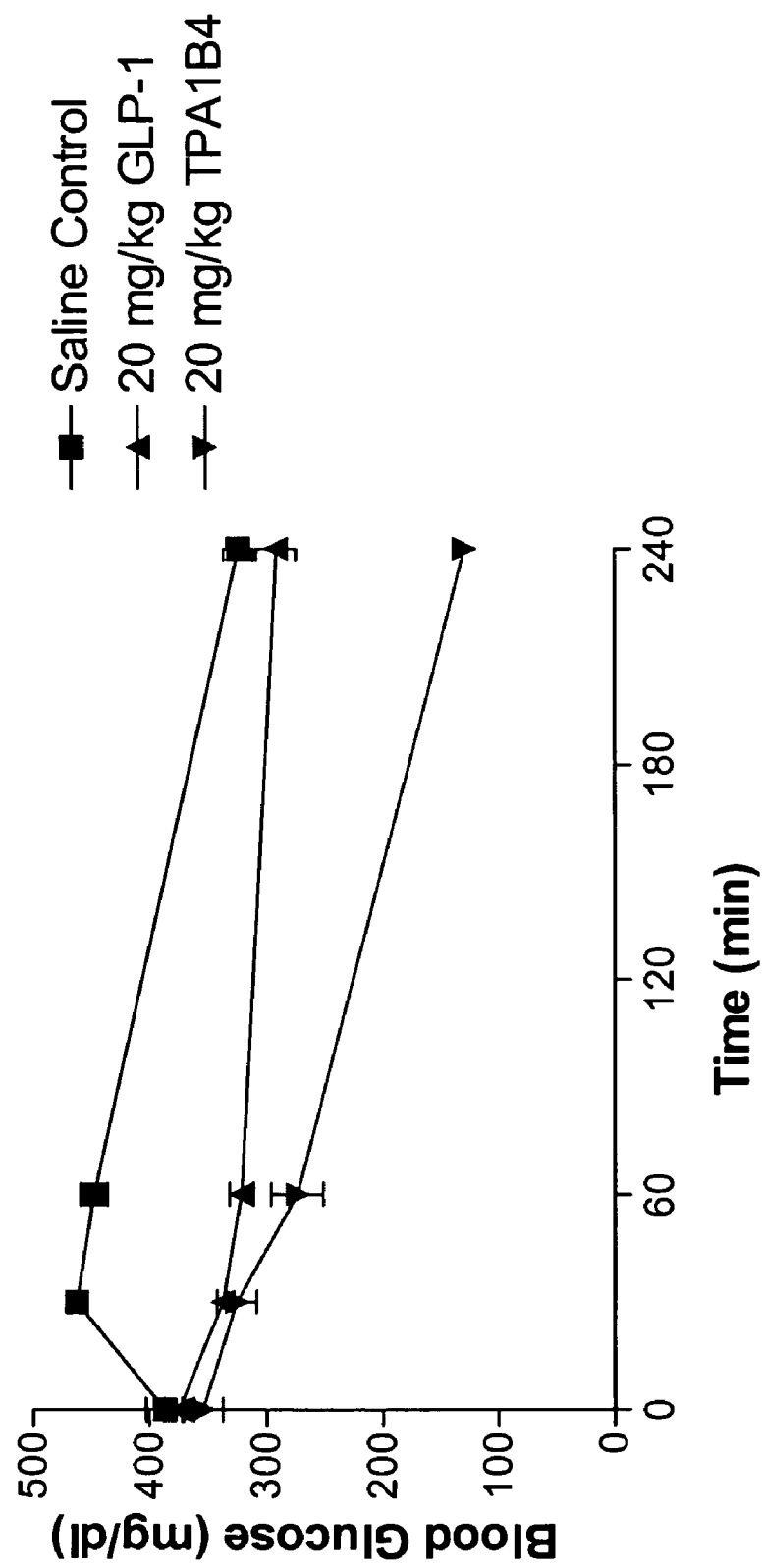
FIG. 12 shows the blood glucose level in diabetic mice for a GLP-1 analog (TPA1B4) at a dose of 20 mg/kg over time compared to the blood glucose level for a saline or GLP-1 control.

FIG. 12 shows the blood glucose level in diabetic mice for a GLP-1 analog (TPA1B4) at a dose of 20 mg/kg over time compared to the blood glucose level for a saline or GLP-1 control.

Female BKS.Cg-m+/_LePr(db)/J mice were purchased at 5-7 weeks of age and allowed to adjust to vivarium conditions for two weeks prior to the start of the experiments. The mice were housed in pressurized, individually ventilated cages. A standard rodent diet was used with food and water provided ad libitum. Blood glucose was measured with a ThereaSense Freestyle blood glucose monitor. The tail vein was nicked with a needle to obtain a small drop of blood (about 10 μL) for each measurement. The mice were fasted for two hours prior to administration of the dose and throughout the experiment. The GLP-1 analog (TPA1B4) and GLP-1 were dissolved in phosphate buffered saline (PBS) and administered by intraperitoneal injection of the indicated dose in 0.4 mL. The saline control for this experiment was a 0.4 mL injection of PBS. Blood glucose measurements were taken t=0, 30 min, 1 h, and 4 h. Values plotted are the average of ten mice.

Figure 13:
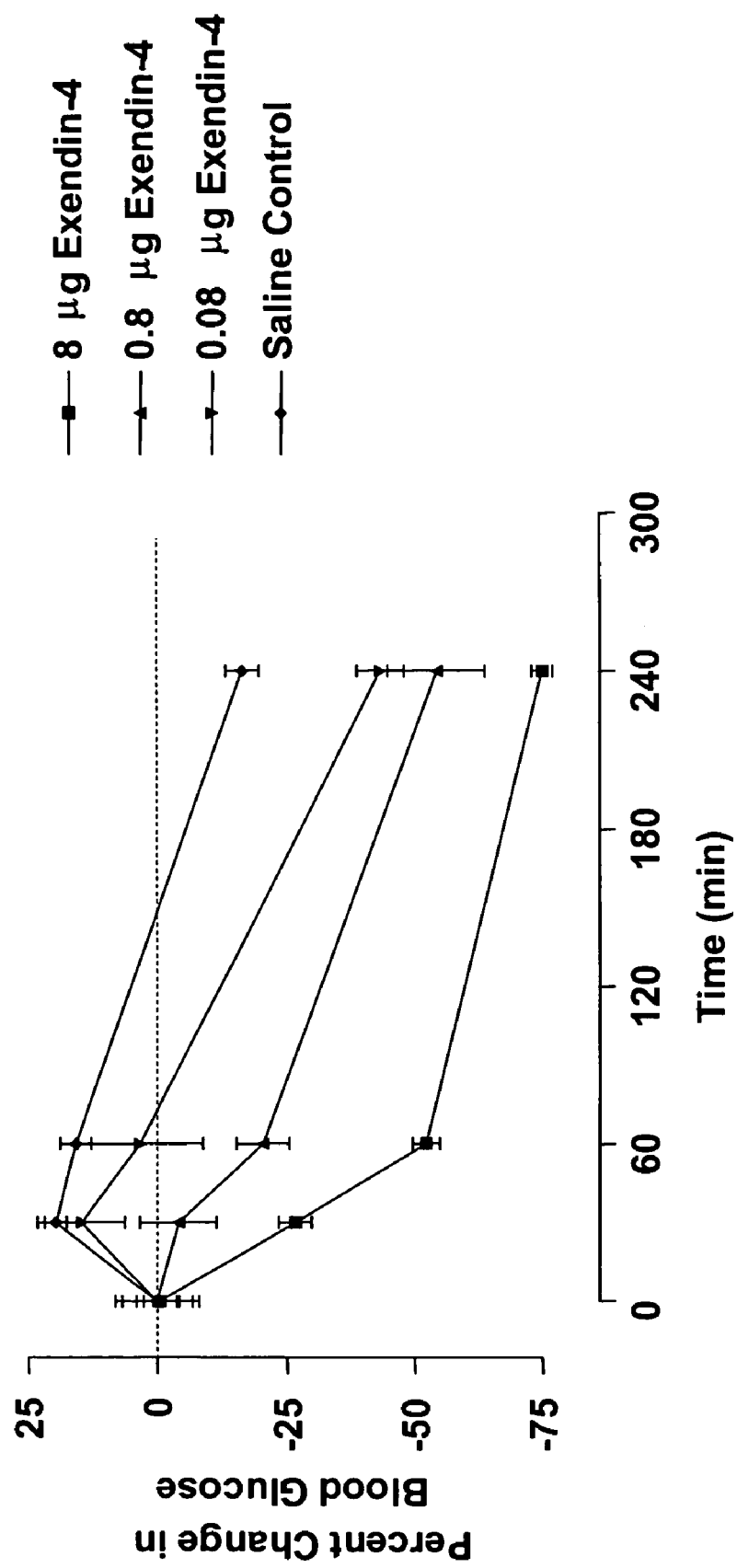
FIG. 13 shows the percent change in blood glucose for Exendin-4 over time for three different doses (8 μg, 0.8 μg, and 0.08 μg) compared to a saline control.

FIG. 13 shows the percent change in blood glucose for Exendin-4 over time for three different doses (8 μg, 0.8 μg, and 0.08 μg) as compared to a saline control.

Figure 14:
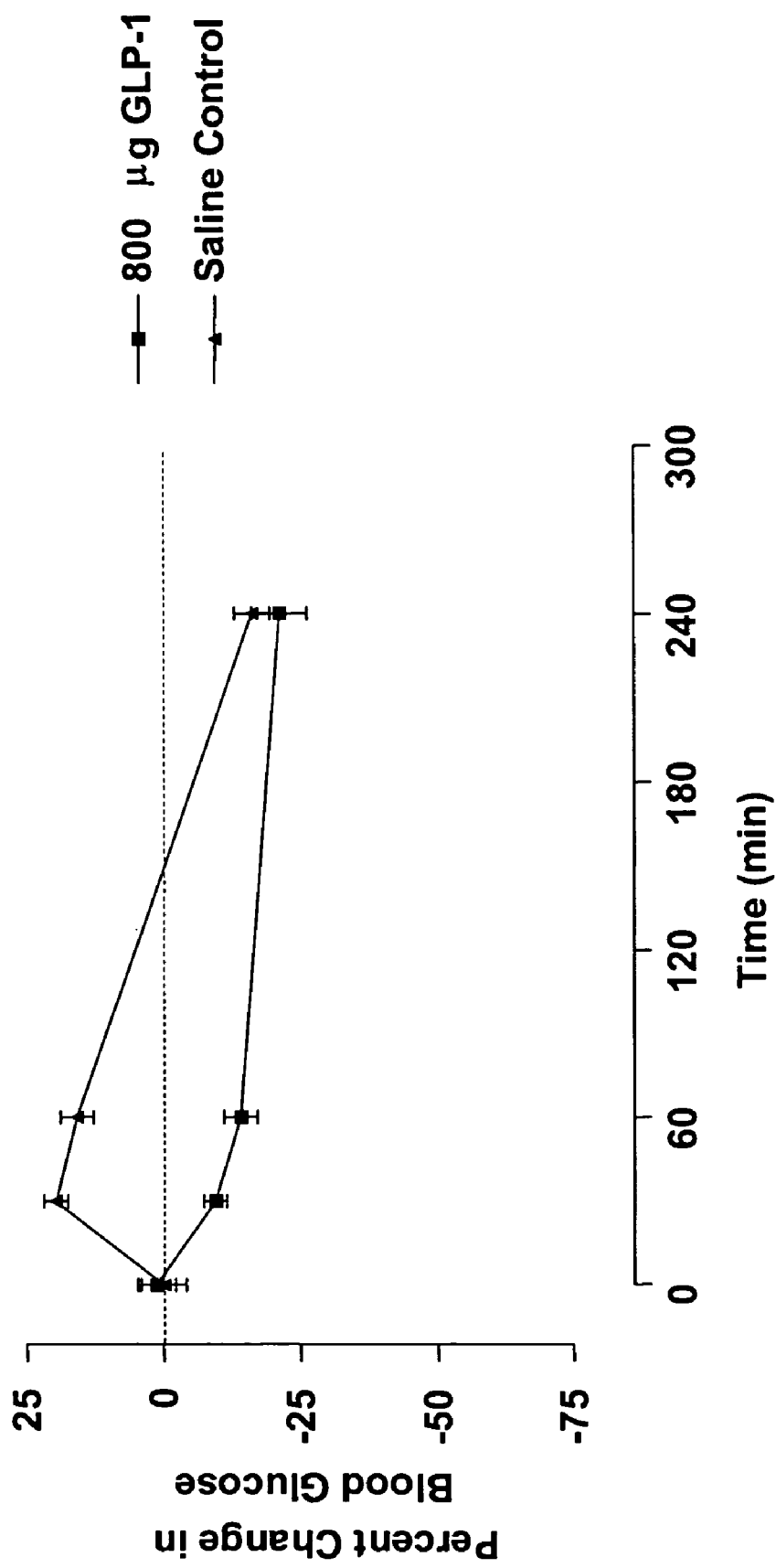
FIG. 14 shows the persent change in blood glucose for GLP-1 over time for a dose of 800 μg compared to a saline control.

FIG. 14 shows the percent change in blood glucose for GLP-1 over time for a dose of 800 μg compared to a saline control.

Figure 15:
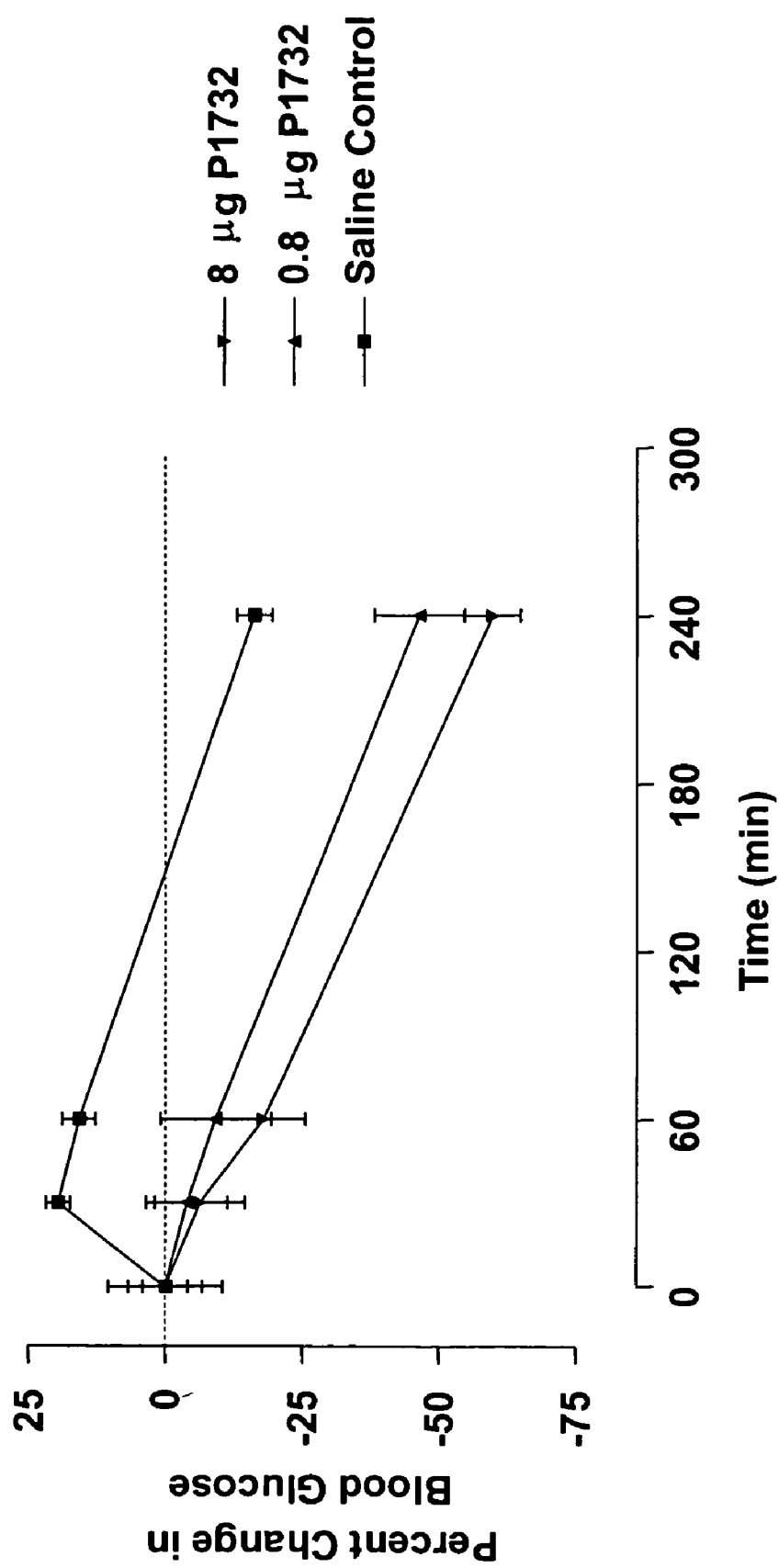
FIG. 15 shows the percent change in blood glucose for a GLP-1 analog (P1732) for two different doses (8 μg and 0.8 μg) as compared to a saline control.

FIG. 15 shows the percent change in blood glucose for a GLP-1 analog (P1732) for two different doses (8 μg and 0.8 μg) as compared to a saline control.

The GLP-1 analog P1732 is an analog of GLP-1 residues 7-36 that incorporates a portion of the Exendin-4 tail with a C-terminal amide and a β-dimethyl aspartate residue at position 9. The sequence for P1732 is:

(SEQ ID NO: 35)
HAXGTFTSDVSSYLEGQAAKEFIAWLVKGRPSSGAPPPS-NH2

In-vivo experiments were performed using female BKS.Cg-m+/_LePr(db)/J mice that were purchased at 5-7 weeks of age and allowed to adjust to vivarium conditions for two weeks prior to the start of experiments. The mice were house in pressurized, individually ventilated cages. A standard rodent diet was used with food and water provided ad libitum. Blood glucose was measured with a ThereaSense Freestyle blood glucose monintor. The tail vein was nicked with a needle to obtain a small drop of blood (~10 μL) for each measurement. The mice were fasted for 2 hours prior to administration of the dose and throughout the experiment. The GLP-1 analog (P1732) was dissolved in phosphate buffered saline (PBS) and administered by intraperitoneal injection of the indicated dose in 0.4 ml. The saline control for this experiment was a 0.4 ml injection of PBS. Blood glucose measurements were made prior to the injection and at 30, 60 and 240 minutes post injection. Values plotted are the average of 5 mice for the P1732 data and 10 mice for the saline control.

FIG. 16 shows exemplary embodiments of Formula (II), wherein naturally occurring amino acids have been modified at the β-position (3-position) with $R_1$ and $R_2$ where $R_1$ and $R_2$ are independently lower alkyl or halogen. In preferred embodiments, $R_1$ and $R_2$ are both lower alkyl. In a more preferred embodiment, $R_1$ and $R_2$ are independently methyl, ethyl, or propyl. In the most preferred embodiment, both $R_1$ and $R_2$ are methyl.

All publications, patents, and patent applications are herein incorporated by reference in their entirety to the same extent as if each individual publication, patent or patent application was specifically and individually indicated to be incorporated by reference in its entirety.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

We claim:

1. A proteinase-resistant analog of GLP-1 with an amino acid sequence represented by:

Xaa-Ala-Yaa-R wherein

Xaa is His;

R is a polypeptide having an amino acid sequence selected from the group consisting of
GTFTSDVSSYLEGQAAKEFIAWLVKGRG,
GTFTSDVSSYLEGQAAKEFIAWLVKGR—NH$_2$,
GTFTSDVSSYLEGQAAKEFIAWLVKGR,
GTFTSDVSSYLEGQAAKEFI-AWLVKGRPSSGAPPPS—NH$_2$, GTFTSDLSKEMEEEAVRLFIEWLKNG-GPSSGAPPPS, and
GTFTSDLSKEMEEEAVRLFIEWLKNG-GPSSGAPPPS—NH$_2$; and Yaa is an amino acid analog of Formula II:

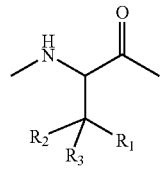

(II)

wherein

R$_1$ and R$_2$ are independently for each occurrence lower alkyl or halogen;

R$_3$ is selected from the group consisting of lower alkyl, aryl, —OH, —(CH$_2$)$_m$—COOH, —(CH$_2$)$_m$—NH$_2$, —(CH$_2$)$_m$—N—C(=NH)NH$_2$, —(CH$_2$)$_m$—C(=O)NH$_2$, —SH, and —(CH$_2$)$_m$—S—CH$_3$; and m is 0, 1, or 2.

2. The proteinase-resistant analog of claim 1, wherein Yaa is an amino acid analog represented by:

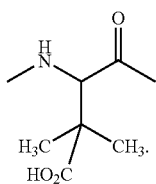

3. The proteinase-resistant analog of claim 1, wherein Yaa is an amino acid analog represented by:

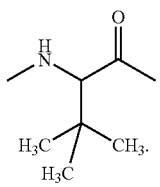

4. A proteinase-resistant analog of a biologically active peptide or polypeptide factor, which peptide or polypeptide factor has the following amino acid sequence:

HAXGTFTSDVSSYLEGQAAKEFIAWLVKGR-NH$_2$ (SEQ ID NO:11)

wherein X is an amino acid analog of Formula II:

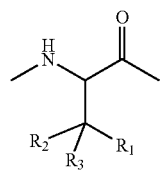

(II)

wherein

R$_1$ and R$_2$ are independently selected from a lower alkyl or a halogen;

R$_3$ is selected from lower alkyl, aryl, hydroxyl group, —(CH$_2$)$_m$—COOH, —(CH$_2$)$_m$—NH$_2$, —(CH$_2$)$_m$—N—C(=NH)NH$_2$, —(CH$_2$)$_m$—C(=O)NH$_2$, —SH, and —(CH$_2$)$_m$—S—CH$_3$; and m is 0, 1, or 2.

5. A proteinase-resistant analog of a biologically active peptide or polypeptide factor, which peptide or polypeptide factor has the following amino acid sequence:

HAXGTFTSDVSSYLEGQAAKEFIAWLVKGRG (SEQ ID NO: 10)

wherein X is an amino acid analog of Formula II:

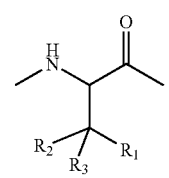

(II)

wherein

R$_1$ and R$_2$ are independently selected from a lower alkyl or a halogen;

R$_3$ is selected from lower alkyl, aryl, hydroxyl group, —(CH$_2$)$_m$—COOH, —(CH$_2$)$_m$—NH$_2$, —(CH$_2$)$_m$—N—C(=NH)NH$_2$, —(CH$_2$)$_m$—C(=O)NH$_2$, —SH, and —(CH$_2$)$_m$—S—CH$_3$; and m is 0, 1, or 2.

6. A proteinase-resistant analog of a biologically active peptide or polypeptide factor, which peptide or polypeptide factor has the following amino acid sequence:

(SEQ ID NO: 36)
HAXGTFTSDVSSYLEGQAAKEFIAWLVKGRPSSGAPPPS-NH$_2$ wherein X is an amino acid analog of Formula II:

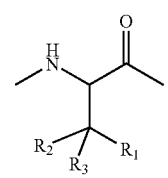

(II)

wherein

R$_1$ and R$_2$ are independently selected from a lower alkyl or a halogen;

R$_3$ is selected from lower alkyl, aryl, hydroxyl group, —(CH$_2$)$_m$—COOH, —(CH$_2$)$_m$—NH$_2$, —(CH$_2$)$_m$—N—C(=NH)NH$_2$, —(CH$_2$)$_m$—C(=O)NH$_2$, —SH, and —(CH$_2$)$_m$—S—CH$_3$; and m is 0, 1, or 2.

* * * * *

UNITED STATES PATENT AND TRADEMARK OFFICE
CERTIFICATE OF CORRECTION

PATENT NO. : 7,259,234 B2  
APPLICATION NO. : 10/847220  
DATED : August 21, 2007  
INVENTOR(S) : William W. Bachovchin et al.

Page 1 of 1

It is certified that error appears in the above-identified patent and that said Letters Patent is hereby corrected as shown below:

In the Claims:

Col. 57, line 2, claim 4, replace "which peptide or polypeptide factor" with --which peptide or polypeptide analog--.

Col. 58, line 2, claim 5, replace "which peptide or polypeptide factor" with --which peptide or polypeptide analog--.

Col. 58, line 2, claim 6, replace "which peptide or polypeptide factor" with --which peptide or polypeptide analog--.

Signed and Sealed this  
Sixth Day of August, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 7,259,234 B2
APPLICATION NO. : 10/847220
DATED : August 21, 2007
INVENTOR(S) : William W. Bachovchin et al.

Page 1 of 1

It is certified that error appears in the above-identified patent and that said Letters Patent is hereby corrected as shown below:

In the Claims:

Column 57, line 51 (Claim 4, line 2) replace "which peptide or polypeptide factor" with --which peptide or polypeptide analog--.

Column 58, line 11 (Claim 5, line 2) replace "which peptide or polypeptide factor" with --which peptide or polypeptide analog--.

Column 58, line 39 (Claim 6, line 2) replace "which peptide or polypeptide factor" with --which peptide or polypeptide analog--.

This certificate supersedes the Certificate of Correction issued August 6, 2013.

Signed and Sealed this
Twenty-seventh Day of August, 2013

Teresa Stanek Rea
*Acting Director of the United States Patent and Trademark Office*

```
                         SEQUENCE LISTING

<160> NUMBER OF SEQ ID NOS: 36

<210> SEQ ID NO 1
   <211> LENGTH: 30
   <212> TYPE: PRT
   <213> ORGANISM: Homo sapiens

<400> SEQUENCE: 1

His Ala Glu Gly Thr Phe Thr Ser Asp Val Ser Ser Tyr Leu Glu Gly
   1               5                   10                  15

Gln Ala Ala Lys Glu Phe Ile Ala Trp Leu Val Lys Gly Arg
               20                  25                  30

<210> SEQ ID NO 2
   <211> LENGTH: 30
   <212> TYPE: PRT
   <213> ORGANISM: Homo sapiens

<400> SEQUENCE: 2

His Ala Glu Gly Thr Phe Thr Ser Asp Val Ser Ser Tyr Leu Glu Gly
   1               5                   10                  15

Gln Ala Ala Lys Glu Phe Ile Ala Trp Leu Val Lys Gly Arg
               20                  25                  30

<210> SEQ ID NO 3
   <211> LENGTH: 33
   <212> TYPE: PRT
   <213> ORGANISM: Homo sapiens

<400> SEQUENCE: 3

His Ala Asp Gly Ser Phe Ser Asp Glu Met Asn Thr Ile Leu Asp Asn
   1               5                   10                  15

Leu Ala Ala Arg Asp Phe Ile Asn Trp Leu Ile Gln Thr Lys Ile Thr
               20                  25                  30

Asp

<210> SEQ ID NO 4
   <211> LENGTH: 42
   <212> TYPE: PRT
   <213> ORGANISM: Homo sapiens

<400> SEQUENCE: 4

Tyr Ala Glu Gly Thr Phe Ile Ser Asp Tyr Ser Ile Ala Met Asp Lys
   1               5                   10                  15

Ile His Gln Gln Asp Phe Val Asn Trp Leu Leu Ala Gln Lys Gly Lys
```

```
                    20                  25                  30

Lys Asn Asp Trp Lys His Asn Ile Thr Gln
        35                  40

<210> SEQ ID NO 5
<211> LENGTH: 36
<212> TYPE: PRT
<213> ORGANISM: Homo sapiens

<400> SEQUENCE: 5

Tyr Pro Ser Lys Pro Asp Asn Pro Gly Glu Asp Ala Pro Ala Glu Asp
 1               5                  10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 6
<211> LENGTH: 27
<212> TYPE: PRT
<213> ORGANISM: Homo sapiens

<400> SEQUENCE: 6

Ala Pro Leu Glu Pro Val Tyr Pro Gly Asp Asn Ala Thr Pro Glu Gln
 1               5                  10                  15

Met Ala Gln Tyr Ala Ala Asp Leu Arg Arg Tyr
            20                  25

<210> SEQ ID NO 7
<211> LENGTH: 36
<212> TYPE: PRT
<213> ORGANISM: Homo sapiens

<400> SEQUENCE: 7

Tyr Pro Ile Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 8
<211> LENGTH: 39
<212> TYPE: PRT
<213> ORGANISM: Homo sapiens

<400> SEQUENCE: 8

His Gly Glu Gly Thr Phe Thr Ser Asp Leu Ser Lys Glu Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Homo sapiens

<400> SEQUENCE: 9

His Ser Asp Gly Thr Phe Thr Ser Asp Leu Ser Lys Gln Met Glu Glu
```

```
                1               5                  10                 15
Glu Ala Val Arg Leu Phe Ile Glu Trp Leu Lys Asn Gly Gly Pro Ser
                20                 25                 30

Ser Gly Ala Pro Pro Ser
          35

<210> SEQ ID NO 10
<211> LENGTH: 31
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 10

His Ala Xaa Gly Thr Phe Thr Ser Asp Val Ser Ser Tyr Leu Glu Gly
 1               5                  10                 15

Gln Ala Ala Lys Glu Phe Ile Ala Trp Leu Val Lys Gly Arg Gly
                20                 25                 30

<210> SEQ ID NO 11
<211> LENGTH: 30
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 11

His Ala Xaa Gly Thr Phe Thr Ser Asp Val Ser Ser Tyr Leu Glu Gly
 1               5                  10                 15

Gln Ala Ala Lys Glu Phe Ile Ala Trp Leu Val Lys Gly Arg
                20                 25                 30

<210> SEQ ID NO 12
<211> LENGTH: 33
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 12

His Ala Xaa Gly Ser Phe Ser Asp Glu Met Asn Thr Ile Leu Asp Asn
 1               5                  10                 15

Leu Ala Ala Arg Asp Phe Ile Asn Trp Leu Ile Gln Thr Lys Ile Thr
                20                 25                 30

Asp

<210> SEQ ID NO 13
<211> LENGTH: 42
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 13

Tyr Ala Xaa Gly Thr Phe Ile Ser Asp Tyr Ser Ile Ala Met Asp Lys
 1               5                  10                 15
```

```
Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 14
<211> LENGTH: 36
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 14

Tyr Pro Xaa Lys Pro Asp Asn Pro Gly Glu Asp Ala Pro Ala Glu Asp
 1               5                  10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 15
<211> LENGTH: 27
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 15

Ala Pro Xaa Glu Pro Val Tyr Pro Gly Asp Asn Ala Thr Pro Glu Gln
 1               5                  10                  15

Met Ala Gln Tyr Ala Ala Asp Leu Arg Arg Tyr
            20                  25

<210> SEQ ID NO 16
<211> LENGTH: 36
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 16

Tyr Pro Xaa Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 17
<211> LENGTH: 39
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 17

His Gly Xaa Gly Thr Phe Thr Ser Asp Leu Ser Lys Glu Met Glu Glu
```

```
                      1               5                  10                 15
Glu Ala Val Arg Leu Phe Ile Glu Trp Leu Lys Asn Gly Gly Pro Ser
                 20                 25                 30

Ser Gly Ala Pro Pro Ser
            35

<210> SEQ ID NO 18
<211> LENGTH: 39
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 18

His Ser Xaa Gly Thr Phe Thr Ser Asp Leu Ser Lys Gln Met Glu Glu
  1               5                  10                 15

Glu Ala Val Arg Leu Phe Ile Glu Trp Leu Lys Asn Gly Gly Pro Ser
                 20                 25                 30

Ser Gly Ala Pro Pro Ser
            35

<210> SEQ ID NO 19
<211> LENGTH: 27
<212> TYPE: PRT
<213> ORGANISM: Homo sapiens

<400> SEQUENCE: 19

Gly Thr Phe Thr Ser Asp Val Ser Ser Tyr Leu Glu Gly Gln Ala Ala
  1               5                  10                 15

Lys Glu Phe Ile Ala Trp Leu Val Lys Gly Arg
                 20                 25

<210> SEQ ID NO 20
<211> LENGTH: 36
<212> TYPE: PRT
<213> ORGANISM: Homo sapiens

<400> SEQUENCE: 20

Gly Thr Phe Thr Ser Asp Val Ser Ser Tyr Leu Glu Gly Gln Ala Ala
  1               5                  10                 15

Lys Glu Phe Ile Ala Trp Leu Val Lys Gly Arg Pro Ser Ser Gly Ala
                 20                 25                 30

Pro Pro Ser
        35

<210> SEQ ID NO 21
<211> LENGTH: 27
<212> TYPE: PRT
<213> ORGANISM: Homo sapiens

<400> SEQUENCE: 21

Gly Thr Phe Thr Ser Asp Val Ser Ser Tyr Leu Glu Gly Gln Ala Ala
  1               5                  10                 15

Lys Glu Phe Ile Ala Trp Leu Val Lys Gly Arg
                 20                 25

<210> SEQ ID NO 22
<211> LENGTH: 30
<212> TYPE: PRT
<213> ORGANISM: Homo sapiens
```

```
<400> SEQUENCE: 22

Gly Ser Phe Ser Asp Glu Met Asn Thr Ile Leu Asp Asn Leu Ala Ala
1               5                   10                  15

Arg Asp Phe Ile Asn Trp Leu Ile Gln Thr Lys Ile Thr Asp
            20                  25                  30

<210> SEQ ID NO 23
<211> LENGTH: 39
<212> TYPE: PRT
<213> ORGANISM: Homo sapiens

<400> SEQUENCE: 23

Gly Thr Phe Ile Ser Asp Tyr Ser Ile Ala Met Asp Lys Ile His Gln
1               5                   10                  15

Gln Asp Phe Val Asn Trp Leu Leu Ala Gln Lys Gly Lys Lys Asn Asp
            20                  25                  30

Trp Lys His Asn Ile Thr Gln
                35

<210> SEQ ID NO 24
<211> LENGTH: 33
<212> TYPE: PRT
<213> ORGANISM: Homo sapiens

<400> SEQUENCE: 24

Lys Pro Asp Asn Pro Gly Glu Asp Ala Pro Ala Glu Asp Met Ala Arg
1               5                   10                  15

Tyr Tyr Ser Ala Leu Arg His Tyr Ile Asn Leu Ile Thr Arg Gln Arg
            20                  25                  30

Tyr

<210> SEQ ID NO 25
<211> LENGTH: 24
<212> TYPE: PRT
<213> ORGANISM: Homo sapiens

<400> SEQUENCE: 25

Glu Pro Val Tyr Pro Gly Asp Asn Ala Thr Pro Glu Gln Met Ala Gln
1               5                   10                  15

Tyr Ala Ala Asp Leu Arg Arg Tyr
            20

<210> SEQ ID NO 26
<211> LENGTH: 33
<212> TYPE: PRT
<213> ORGANISM: Homo sapiens

<400> SEQUENCE: 26

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 27
<211> LENGTH: 44
<212> TYPE: PRT
<213> ORGANISM: Homo sapiens

<400> SEQUENCE: 27
```

```
Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40
```

<210> SEQ ID NO 28
<211> LENGTH: 41
<212> TYPE: PRT
<213> ORGANISM: Homo sapiens

<400> SEQUENCE: 28

```
Ala Ile Phe Thr Asn Ser Tyr Arg Lys Val Leu Gly Gln Leu Ser Ala
 1               5                  10                  15

Arg Lys Leu Leu Gln Asp Ile Met Ser Arg Gln Gln Gly Glu Ser Asn
            20                  25                  30

Gln Glu Arg Gly Ala Arg Ala Arg Leu
        35                  40
```

<210> SEQ ID NO 29
<211> LENGTH: 31
<212> TYPE: PRT
<213> ORGANISM: Homo sapiens

<400> SEQUENCE: 29

```
His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30
```

<210> SEQ ID NO 30
<211> LENGTH: 30
<212> TYPE: PRT
<213> ORGANISM: Homo sapiens

<400> SEQUENCE: 30

```
His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30
```

<210> SEQ ID NO 31
<211> LENGTH: 28
<212> TYPE: PRT
<213> ORGANISM: Homo sapiens

<400> SEQUENCE: 31

```
His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys
            20                  25
```

<210> SEQ ID NO 32
<211> LENGTH: 27
<212> TYPE: PRT
<213> ORGANISM: Homo sapiens

<400> SEQUENCE: 32

```
His Ala Glu Gly Thr Phe Thr Ser Asp Val Ser Ser Tyr Leu Glu Gly
 1               5                  10                  15
```

```
Gln Ala Ala Lys Glu Phe Ile Ala Trp Leu Val
            20                  25

<210> SEQ ID NO 33
<211> LENGTH: 9
<212> TYPE: PRT
<213> ORGANISM: Homo sapiens

<400> SEQUENCE: 33

Trp Ala Leu Ala Pro Arg Ser Phe Ala
1               5

<210> SEQ ID NO 34
<211> LENGTH: 9
<212> TYPE: PRT
<213> ORGANISM: Homo sapiens
<220> FEATURE:
<221> NAME/KEY: ACT_SITE
<222> LOCATION: 7
<223> OTHER INFORMATION: Xaa = Any Amino Acid

<400> SEQUENCE: 34

Trp Ala Leu Ala Pro Arg Xaa Phe Ala
1               5

<210> SEQ ID NO 35
<211> LENGTH: 30
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 35

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 36
<211> LENGTH: 39
<212> TYPE: PRT
<213> ORGANISM: Homo sapiens
<220> FEATURE:
<221> NAME/KEY: ACT_SITE
<222> LOCATION: 3
<223> OTHER INFORMATION: Xaa = Any Amino Acid

<400> SEQUENCE: 36

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Ser
            35
```